(12) United States Patent
Niestroj et al.

(10) Patent No.: US 7,667,044 B2
(45) Date of Patent: Feb. 23, 2010

(54) COMPOUNDS FOR THE TREATMENT OF NEUROLOGICAL DISORDERS

(75) Inventors: André Niestroj, Sennewitz (DE); Ulrich Heiser, Halle/Saale (DE); Ingo Schulz, Halle/Saale (DE); Jens-Ulrich Rahfeld, Lieskau (DE); Joachim Baer, Halle/Saale (DE); Hans-Ulrich Demuth, Halle/Saale (DE)

(73) Assignee: Probiodrug AG, Halle/Saale (DE)

( * ) Notice: Subject to any disclaimer, the term of this patent is extended or adjusted under 35 U.S.C. 154(b) by 737 days.

(21) Appl. No.: 11/290,735

(22) Filed: Nov. 30, 2005

(65) Prior Publication Data

US 2006/0100253 A1    May 11, 2006

Related U.S. Application Data

(63) Continuation-in-part of application No. 11/002,169, filed on Dec. 2, 2004.

(60) Provisional application No. 60/516,717, filed on Nov. 3, 2003, provisional application No. 60/684,137, filed on May 24, 2005.

(51) Int. Cl.
| | |
|---|---|
| C07D 277/00 | (2006.01) |
| C07D 207/00 | (2006.01) |
| C07D 295/00 | (2006.01) |
| C07D 409/00 | (2006.01) |
| C07D 411/00 | (2006.01) |
| A01N 43/78 | (2006.01) |
| A01N 43/36 | (2006.01) |
| A61K 31/425 | (2006.01) |
| A61K 31/40 | (2006.01) |

(52) U.S. Cl. ............... 548/200; 548/518; 548/530; 548/527; 514/365; 514/423

(58) Field of Classification Search ............ 548/200, 548/518, 530, 527; 514/365, 423
See application file for complete search history.

(56) References Cited

U.S. PATENT DOCUMENTS

| 5,547,978 | A | 8/1996 | Christensen et al. ........ 514/422 |
| 7,371,871 | B2 | 5/2008 | Schilling | |
| 7,381,537 | B2 | 6/2008 | Demuth | |
| 7,462,599 | B2 | 12/2008 | Schilling | |
| 2005/0171112 | A1 | 8/2005 | Schulz et al. ............ 514/249 |
| 2007/0191366 | A1 | 8/2007 | Hoffmann | |
| 2008/0153892 | A1 | 6/2008 | Schilling | |
| 2008/0286810 | A1 | 11/2008 | Demuth | |
| 2009/0068699 | A1 | 3/2009 | Schilling | |
| 2009/0149394 | A1 | 6/2009 | Schilling | |

FOREIGN PATENT DOCUMENTS

| EP | 0 154 353 | 9/1985 |
| EP | 0 201 741 | 11/1986 |
| WO | WO 95/22327 | 8/1995 |
| WO | WO 01/34594 | 5/2001 |
| WO | WO 03/040174 | 5/2003 |
| WO | WO 2004/098591 | 11/2004 |
| WO | WO 2005/075436 | 8/2005 |
| WO | WO 2005/103043 | 11/2005 |

OTHER PUBLICATIONS

Database Beilstein; Data Accession Nos. 580461, 4016039 (XP002378930); vol. 642, 1961, pp. 133-140.
Database Beilstein; Data Accession Nos. 8498197, 8498907, 8507776, 8508303 (XP002378931); vol. 55, 1999, pp. 15001-15010.
Database Beilstein; Data Accession No. 8589072 (XP002378932); vol. 1, 2001, pp. 113-120.
Database Beilstein; Data Accession No. 9878605 (XP002378933); vol. 11, 2004, pp. 1806-1813.
Database Beilstein; Data Accession Nos. 9878207, 9878604 (XP002378934); vol. 16, 2004, pp. 2645-2652.
Database Beilstein; Data Accession No. 5913897 (XP002378935); vol. 34(2), 1993, pp. 211-214.
Database Beilstein; Data Accession No. 6678654 (XP002378936); vol. 35(4), 1994, pp. 591-594.
Database Beilstein; Data Accession No. 8528734 (XP002378937); vol. 10(1), 2000, pp. 45-48.
Database Beilstein; Data Accession No. 8462536 (XP002378938); vol. 117(5), 1996, pp. 986-992.
Joyeau, et al.; "Synthesis and activity of pyrrolidinyl- and thiazolidinyl-dipeptidase derivatives as inhibitors of the Tc80 prolyl oligopeptidase from Trypanosoma cruzi"; *Eur. J. Med. Chem.*; 2000; 35: 257-266.
Ferraris, et al.; "Ketopyrrolidines and ketoazetidines as potent dipeptidyl peptidase IV (DPP IV) inhibitors"; *Bioorganic & Medicinal Chemistry Letters*; 2004; 14: 5579-5583.
De Nanteuil, et al.; "Prolyl endopeptidase inhibitors: a new class of memory enhancing drugs"; *Drugs of the Future*; 1998; 23(2): 167-179.
Tsutsumi, et al.; "•-Ketothiazole Inhibitors of Prolyl Endopeptidase"; *Bioorganic & Medicinal Chemistry Letters*; 1994; 4(6): 831-834.
Tsutsumi, et al.; "Synthesis and Structure-Activity Relationships of Peptidyl alpha-Keto Heterocycles as Novel Inhibitors of Prolyl endopeptidase"; *J. Med. Chem.*; 1994; 37(21): 3492-3502.
Tsutsumi, et al.; "Prolyl Endopeptidase Inhibitors II. A peptidyl alpha-Keto Thiazole Derivative"; *ACTA Cryst.*; 1995; C51: 1925-1927.
International Search Report for Application No. PCT/EP2005/012765 date of completion May 4, 2006.

*Primary Examiner*—Sreeni Padmanabhan
*Assistant Examiner*—Kara R McMillian
(74) *Attorney, Agent, or Firm*—Sonnenschein Nath & Rosenthal LLP

(57) ABSTRACT

The present invention relates to novel inhibitors of prolyl endopeptidase of formula 1

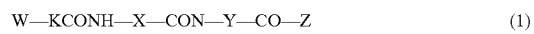

wherein K, W, X, Y and Z are specified in the description.

Figure 1:
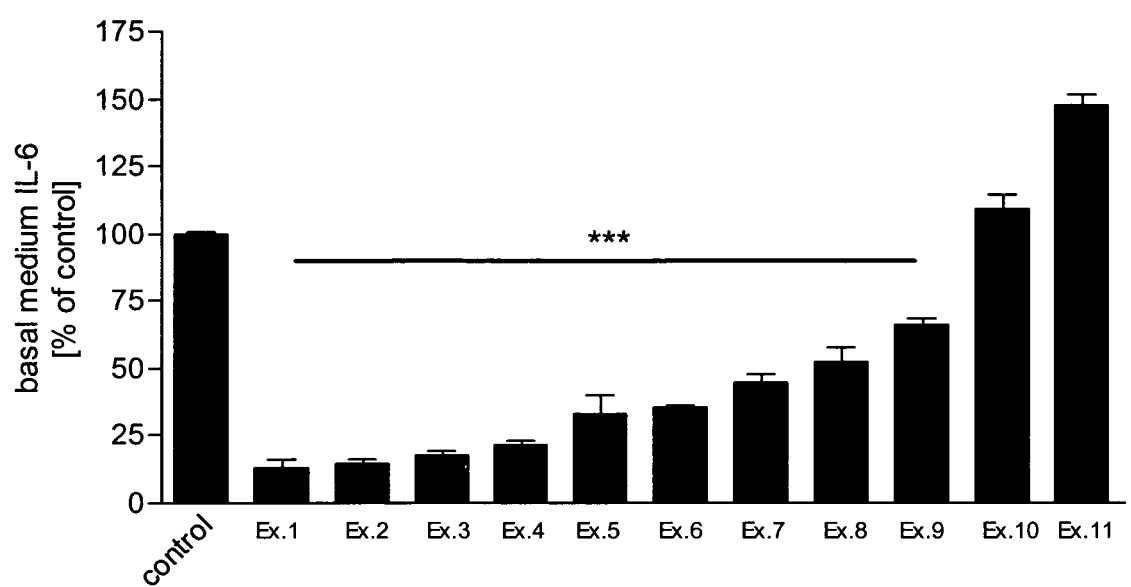

The compounds are useful for the treatment of diseases such as mild cognitive impairment (MCI), Alzheimer's disease, Down Syndrome, Parkinson disease and Chorea Huntington.

45 Claims, 9 Drawing Sheets

COMPOUNDS FOR THE TREATMENT OF NEUROLOGICAL DISORDERS

RELATED APPLICATIONS

This application is a Continuation-in-Part of U.S. Ser. No. 11/002,169 filed Dec. 2, 2004, which claims priority to U.S. Ser. No. 10/976,677 filed on Oct. 29, 2004, which claims priority under 35 U.S.C. §119(e) to U.S. Provisional Application No. 60/516,717 filed on Nov. 3, 2003, the entirety of which are incorporated herein by reference. This application also claims priority under 35 U.S.C. §119(e) to U.S. Provisional Application No. 60/684,137 filed on May 24, 2005.

FIELD OF THE INVENTION

This invention relates to heteroaryl-carbonyl compounds as inhibitors of prolyl endopeptidase (PEP, EC 3.4.21.26) and PEP-like enzymes.

BACKGROUND OF THE INVENTION

Prolyl endopeptidase (PEP; EC 3.4.21.26; also called prolyl oligopeptidase) is a serine peptidase characterized by oligopeptidase activity. It is the name given to enzymes of family S9A, prolyl oligopeptidases, in clan SC (1). Enzymes belonging to clan SC are distinct from trypsin- or subtilisin-type serine peptidases by structure and by order of the catalytic triad residues in the primary sequence (2;3). The recently reported three dimensional structure of PEP revealed a two domain organization (4). The catalytic domain displays an α/β hydrolase fold in which the catalytic triad (Ser554, His680, Asp641) is covered by a so-called β-propeller domain. Most likely, the propeller domain controls the access of potential substrates to the active site of the enzyme and excludes peptides having more than 30 amino acids.

Despite a profound knowledge of the enzymatic and structural properties of PEP, the biological function of this enzyme is far from being fully understood (5;6). Highly conserved in mammals, PEP is ubiquitously distributed, with high concentrations occurring in the brain (7). Recently, the enzyme gained pharmaceutical interest due to a reported cognitive enhancement induced by treatment with specific PEP inhibitors. In rats displaying scopolamine-induced amnesia, PEP inhibition caused acetylcholine release in the frontal cortex and hippocampus (8). Furthermore, administration of a PEP inhibitor in rats with middle cerebral artery occlusion prolonged passive avoidance latency and reduced the prolonged escape latency in the Morris water maze task (9). The potential of PEP inhibitors as antidementia drugs was further confirmed by reports of neuroprotective effects. Inducing neurodegeneration in cerebellar granule cells led to increased neuronal survival and enhanced neurite outgrowth in presence of a PEP inhibitor (10). Moreover, the level of $m_3$-muscarinic acetylcholine receptor mRNA was found to be increased after PEP inhibition. This resulted in a stimulated phosphoinositide turnover.

It has been hypothesized that these effects are due to modulation of neuropeptide bioactivity by PEP (11). In vitro, PEP is able to rapidly inactivate several neuropeptides, including substance P and arginine-vasopressin (AVP) by limited proteolysis (12;13). Neuropeptides, such as substance P or AVP are known to influence learning and memory (14;15). The administration of substance P can induce long-term potentiation (LTP), a well established parameter for learning and memory (16). Binding of substance P to neurokinin 1 receptor stimulates a G-protein mediated increase in $IP_3$ concentration and a release of $Ca^{2+}$ from intracellular stores within the endoplasmic reticulum (ER) (17;18). It is well established, but untested for substance P, that $Ca^{2+}$ release from these stores is implicated in the induction of LTP and in learning and memory (19). In postsynaptic cells, LTP is prevented by the inhibition of $IP_3$ receptors, demonstrating the crucial role of $IP_3$ formation and $Ca^{2+}$ release in this learning and memory model (20). It should be noted, however, that PEP is primarily located in the cytosol (21), whereas the interaction between the neuropeptides and their receptors takes place on the cell surface. Recently, Hasebe et al. found, that cytosolic prolyl endopeptidase is involved in the degradation of p40-phox splice variant protein in myeloid cells (22).

EP 0 172 458 discloses N-phenyl alkanoyl pyrrolidine derivatives useful as anti-amnesic agents.

EP 0 359 547 discloses pyridine compounds inhibiting prolylendo peptidase activity and useful for the treatment of amnesia.

U.S. Pat. No. 5,340,832 discloses N-substituted carbamoyl-alkanoyl-prolinal derivatives useful as inhibitors of prolyl endopeptidase for treating amnesia.

U.S. Pat. No. 5,763,576 discloses tetrapeptide alpha-ketoamides as selective and total inhibitors of serine and cysteine proteases. These compounds are useful in the treatment of tissue damage and various inflammatory conditions, such as blistering, and in the treatment of neurodegenerative diseases such as ischemia, stroke and Alzheimer's disease. The compounds are also inhibitors for blood coagulation enzymes and are useful anticoagulants for the treatment of thrombosis.

WO 91/18891 discloses aromatic pyrrolidine and thiazolidine amide(s) as prolyl endopeptidase inhibitors, which are useful for treating CNS disorders such as various memory or learning dysfunctions associated with disease e.g. Alzheimer's disease; amnesia; dementia; anxiety; ischemia; and damage caused by stroke.

WO 94/12474 discloses cyclic ketone compounds as prolyl endopeptidase inhibitors—including two nitrogen-containing heterocycles linked by a carbonyl group. These compounds inhibit the degradation and deactivation of TRH, substance P, neurotensin and vasopressin. They are useful for the treatment and prevention of amnesia and of dementia including Alzheimer's disease.

WO 95/03277 discloses N-substituted pyrrolidinyl-oxoacetamide compounds as protease (especially PEP) inhibitors useful for treating memory loss e.g. Alzheimer's disease, and auto-immune disorders.

WO 95/15310 discloses prolyl peptide derivatives as prolyl endopeptidase inhibitors. These compounds can be used as memory enhancing agents to improve mental capacity, ability to recall cognitive events, and learned motor activities. Thus the compounds of WO 95/15310 may be used in patients suffering from aphasia, apraxia, agnosia, or any type of amnesias, benign forgetfulness and Korsakoff's syndrome. The compounds may also be used to prevent or slow memory deficits.

WO 97/07116 discloses PEP inhibitors for the use in treatment of acute events (such as ischemia and hypoxia) and progressive neurodegenerative disorders, including Alzheimer's disease, AIDS dementia and Huntington's disease.

WO 98/35960 discloses PEP inhibitors useful as nootropics having memory enhancing and anti-amnesic effects useful in the treatment of age-related cognitive decline and neuroprotectants useful for treatment of acute events (ischemia/hypoxia) and progressive neurodegenerative disorders such as Alzheimer's disease, AIDS related dementia and Huntington's disease.

WO 00/09542 discloses alpha-keto heterocycles inhibiting the enzymatic activity of a serine proteases. The compounds can be used to inhibit microbial growth, reduce perioperative blood loss, preserve transplantation tissues or organs, inhibit cancer cell growth or tumor progression or tumor metastasis or invasion, treat pulmonary vascular disease, restenosis or pulmonary hypertension myocarditis, bronchopulmonary dysplasia, myocardial necrosis or post-cardiac transplant coronary arteriopathy, atherosclerosis, reperfusion injury, Alzheimer's disease, hypoxia, ischemia and blood coagulation disorders.

U.S. Pat. No. 5,547,978 discloses PEP inhibitors based on pyrrolidin-2-ylcarbonylheterocyclic compounds, they can be used to inhibit PEP in mammalian brain for a pharmaceutical effect.

US2005/0171112 discloses the PEP inhibitor ZW215.

REFERENCES

1. Handbook of Proteolytic Enzymes (1998). Barrett, A. J., Rawlings, N. D., and Woessner, J. F. London, Academic Press.
2. Goossens, F., De, M., I, Vanhoof, G., Hendriks, D., Vriend, G., and Scharpe, S. (1995) *Eur. J. Biochem.* 233, 432-441
3. Barrett, A. J. and Rawlings, N. D. (1992) *Biol. Chem. Hoppe Seyler* 373, 353-360
4. Fulop, V., Bocskei, Z., and Polgar, L. (1998) *Cell* 94, 161-170
5. Wetzel, W., Wagner, T., Vogel, D., Demuth, H. U., and Balschun, D. (1997) *Neuropeptides* 31, 41-45
6. Demuth, H. U., Neumann, U., and Barth, A. (1989) *J. Enzyme Inhib.* 2, 239-248
7. Goossens, F., De, M., I, Vanhoof, G., and Scharpe, S. (1996) *Eur. J. Clin. Chem. Clin. Biochem.* 34, 17-22
8. Toide, K., Iwamoto, Y., Fujiwara, T., and Abe, H. (1995) *J. Pharmacol. Exp. Ther.* 274, 1370-1378
9. Shinoda, M., Matsuo, A., and Toide, K. (1996) *Eur. J. Pharmacol.* 305, 31-38
10. Katsube, N., Sunaga, K., Aishita, H., Chuang, D. M., and Ishitani, R. (1999) *J. Pharmacol. Exp. Ther.* 288, 6-13
11. Shishido, Y., Furushiro, M., Tanabe, S., Shibata, S., Hashimoto, S., and Yokokura, T. (1999) *Eur. J. Pharmacol.* 372, 135-142
12. Mentlein, R. (1988) *FEBS Lett.* 234, 251-256
13. Wilk, S. (1983) *Life Sci.* 33, 2149-2157
14. Bennett, G. W., Ballard, T. M., Watson, C. D., and Fone, K. C. (1997) *Exp. Gerontol.* 32, 451-469
15. Huston, J. P. and Hasenohrl, R. U. (1995) *Behav. Brain Res.* 66, 117-127
16. Liu, X. G. and Sandkuhler, J. (1998) *Neuroscience* 86, 1209-1216
17. Abdel-Latif, A. A. (1989) *Life Sci.* 45, 757-786
18. Defea, K., Schmidlin, F., Dery, O., Grady, E. F., and Bunnett, N. W. (2000) *Biochem. Soc. Trans.* 28, 419-426
19. Voronin, L., Byzov, A., Kleschevnikov, A., Kozhemyakin, M., Kuhnt, U., and Volgushev, M. (1995) *Behav. Brain Res.* 66, 45-52
20. Komatsu, Y. (1996) *J. Neurosci.* 16, 6342-6352
21. Kimura, A., Yoshida, I., Takagi, N., and Takahashi, T. (1999) *J. Biol. Chem.* 274, 24047-24053
22. Hasebe, T., Hua, J., Someya, A., Morain, P., Checler, F., and Nagaoka, I. (2001) *J. Leu. Biol.* 69, 963-968
23. Bodanszky, M. and Bodanszky, A. (1994) *The practice of peptide synthesis*, 2$^{nd}$ Edition; Springer-Verlag: Berlin Heidelberg
24. Tietze, L. F. and Eicher, Th. (1981) *Reaktionen und Synthesen im organisch-chemisches Grundpraktikum*; Georg Thieme Verlag Stuttgart
25. Yasuma, T.; Oi, S.; Choh, N.; Nomura, T.; Furuyama, N.; Nishimura, A.; Fujisawa, Y.; and Sohda, T. (1998) *J Med Chem* 41, 4301-4308
26. Devianne, G.; Escudier, J.-M.; Baltas, M.; and Gorrichon, L. (1995) *J. Org. Chem.* 7343-7347
27. Guo, B., Zhai, D., Cabezas, E., Welsh, K., Nouraini, S., Satterthwait, A. C., and Reed, J. C. (2003) *Nature* 423, 456-461.
28. Ikonen, M., Liu, B., Hashimoto, Y., Ma, L., Lee, K. W., Niikura, T., Nishimoto, I., and Cohen, P. (2003) *Proc. Natl. Acad. Sci. U.S.A* 100, 13042-13047.
29. Sponne, I., Fifre, A., Koziel, V., Kriem, B., Oster, T., and Pillot, T. (2004) *Mol. Cell Neurosci.* 25, 95-102.
30. Hashimoto, Y., Niikura, T., Tajima, H., Yasukawa, T., Sudo, H., Ito, Y., Kita, Y., Kawasumi, M., Kouyama, K., Doyu, M., Sobue, G., Koide, T., Tsuji, S., Lang, J., Kurokawa, K., and Nishimoto, I. (2001) *Proc. Natl. Acad. Sci. U.S.A* 98, 6336-6341.
31. Kariya, S., Takahashi, N., Hirano, M., and Ueno, S. (2003) *Mol. Cell Biochem.* 254, 83-89.
32. Hashimoto, Y., Ito, Y., Niikura, T., Shao, Z., Hata, M., Oyama, F., and Nishimoto, I. (2001) *Biochem. Biophys. Res. Commun.* 283, 460-468.
33. Tajima, H., Niikura, T., Hashimoto, Y., Ito, Y., Kita, Y., Terashita, K., Yamazaki, K., Koto, A., Aiso, S., and Nishimoto, I. (2002) *Neurosci. Lett.* 324, 227-231.
34. Hashimoto, Y., Niikura, T., Ito, Y., Sudo, H., Hata, M., Arakawa, E., Abe, Y., Kita, Y., and Nishimoto, I. (2001) *J. Neurosci.* 21, 9235-9245.
35. Yamagishi, Y., Hashimoto, Y., Niikura, T., and Nishimoto, I. (2003) *Peptides* 24, 585-595.
36. Tsutsumi, S.; Okonogi, T.; Shibahara, S.; Ohuchi, S.; Hatsushiba, E.; Patchett, A. A.; and Christensen, B. G. (1994) *J Med Chem* 37, 3492-3502

DEFINITIONS

The term "PEP-inhibitor" or "prolyl endopeptidase inhibitor" is generally known to a person skilled in the art and means enzyme inhibitors which inhibit the catalytic activity of prolyl endopeptidase (PEP, prolyl oligopeptidase, POP).

"PEP activity" is defined as the catalytic activity of an endoprotease that is capable to hydrolyze post proline bonds in peptides or proteins where the proline is in amino acid position 3 or higher counted from the N-terminus of a peptide or protein substrate.

"PEP-like enzymes" are enzymatically active proteins or peptides, which have PEP activity and are thereby inhibited by PEP-inhibitors.

As used herein, the term "pharmaceutically acceptable" embraces both human and veterinary use: for example the term "pharmaceutically acceptable" embraces a veterinarily acceptable compound or a compound acceptable in human medicine and health care.

Throughout the description and the claims the expression "acyl", unless specifically limited, denotes a $C_{1-12}$ acyl residue, preferably a $C_{1-8}$ acyl residue and especially preferred a $C_{1-4}$ acyl residue. Examples of acyl include alkanoyl groups mentioned below and benzoyl.

Throughout the description and the claims the expression "alkyl", unless specifically limited, denotes a $C_{1-12}$ alkyl group, preferably a $C_{1-6}$ alkyl group. Alkyl groups may be straight chain or branched. Suitable alkyl groups include, for example, methyl, ethyl, propyl (e.g. n-propyl and isopropyl), butyl (e.g. n-butyl, tert-butyl and sec-butyl), pentyl, hexyl, heptyl (e.g. n-heptyl) and octyl (e.g. n-octyl). The expression "alk", for example in the expression "alkoxy", and the expression "alkan", for example in the expression "alkanoyl", should be interpreted in accordance with the definition of "alkyl". Exemplary alkoxy groups include methoxy, ethoxy, butoxy (e.g. n-butoxy), heptyloxy (e.g. n-heptyloxy) and octyloxy (e.g. n-octyloxy). Exemplary alkanoyl (i.e. acyl groups) include ethanoyl (i.e. acetyl), propionyl and butyryl.

The expression "alkenyl", unless specifically limited, denotes a $C_{2-12}$ alkenyl group, preferably a $C_{2-6}$ alkenyl group, which contains at least one double bond at any desired location. Alkenyl groups may be straight chain or branched. Exemplary alkenyl groups include ethenyl, propenyl and butenyl.

The expression "alkynyl", unless specifically limited, denotes a $C_{2-12}$ alkynyl group, preferably a $C_{2-6}$ alkynyl group, which contains at least one triple bond at any desired location. Alkynyl groups may be straight chain or branched. Exemplary alkenyl groups include ethynyl, propynyl and butynyl.

The expression "cycloalkyl", unless specifically limited, denotes a $C_{3-12}$ cycloalkyl group, typically a $C_{3-8}$ cycloalkyl group. Exemplary cycloalkyl groups include cyclopropyl, cyclobutyl, cyclopentyl, cyclohexyl, cycloheptyl and cyclooctyl. Cycloalkyl groups may be branched in which case the number of carbons indicates the total number of carbons in the moiety. A group such as cyclopentylmethyl- which contains a cycloalkyl group linked to alkylene is also embraced by the definition of "cycloalkyl", in which case the number of carbons indicates the total number of carbons in the moiety.

Alkyl groups including derivatives such as alkoxy together with alkenyl, alkynyl and cycloalkyl groups may optionally be halogen substituted e.g. substituted by fluoro. For example, halo substituted alkyl groups include trifluoromethyl and halo substituted alkoxy groups include trifluoromethoxy.

The term "halogen" comprises fluorine (—F), chlorine (—Cl), bromine (—Br), and iodine (—I).

The expression "carbocyclic" or "carbocycle", unless specifically limited, denotes a carbocyclic group containing between 3 and 12 carbon atoms, more typically between 3 and 8 carbon atoms, which may optionally be branched. A carbocyclic group, as used herein, refers to a group other than aryl or cycloalkyl which comprises at least one ring of carbon atoms without heteroatoms. Examples of carbocylic groups include bridged ring systems (e.g. bicyclo[2.2.1]heptenyl) and partially unsaturated ring systems (e.g. cyclohexenyl). Such groups may be optionally substituted e.g. by alkyl, halo, oxo or hydroxyl.

The expression "heterocyclic" or "heterocycle", unless specifically limited, denotes a cycloalkyl residue or carbocylic residue, wherein one or more (e.g. 1, 2 or 3) ring atoms are replaced by heteroatoms selected from N, S or O. Exemplary heterocyclic groups containing one hetero atom include pyrrolidine, tetrahydrofuran and piperidine. Exemplary heterocyclic groups containing two hetero atoms include morpholine and piperazine. Such groups may be optionally substituted e.g. by alkyl (eg methyl), halo, oxo or hydroxyl.

Further examples of heterocyclic groups include oxirane (oxacyclopropane), aziridine (azacyclopropane), thiirane, oxetane, azetidine, thietane, thiolane, 1,3-dioxolane, thiazolidine, imidazolidine, oxazolidine, pyrazolidine, tetrahydropyran and piperazine. Another example of a heterocycle is urotropine. Other heterocyclic groups include lactams, lactones, cyclic imides and cyclic anhydrides. Examples of substituted heterocyclic groups include 1,1-dioxo-thiolane, N-methyl-piperazine, 2-(N-methyl)-N'-piperazinyl)-ethyl, 4-N-(2'-hydroxyethyl)-1-N-piperazinyl and 2-(N-morpholino)-ethyl.

The expression "aryl", unless specifically limited, denotes a $C_{6-12}$ aryl group, preferably a $C_{6-8}$ aryl group. Aryl groups will contain at least one aromatic ring (e.g. one, two or three rings), but may also comprise partially or fully unsaturated rings. An example of an aryl group with one aromatic ring is phenyl. Examples of aromatic groups with two aromatic rings include naphthyl (e.g. 1-naphthyl-, or 2-naphthyl-). Other aryl groups include 1-anthracenyl-, 2-anthracenyl- and 3-anthracenyl-. Examples of aryl groups which contain partially or fully unsaturated rings include tetralin and indene. A most typical aryl group is phenyl.

The expression "heteroaryl", unless specifically limited, denotes as an aryl residue, wherein one or more (e.g. 1, 2, 3, or 4, preferably 1, 2 or 3) ring atoms are replaced by heteroatoms selected from N, S and O or else a 5-membered aromatic ring containing one or more (e.g. 1, 2, 3, or 4, preferably 1, 2 or 3) ring atoms selected from N, S and O. As noted below, heteroaryl groups may optionally be substituted. Exemplary heteroaryl groups include, pyridine (e.g. 2-, 3- or 4-pyridine), pyrimidine, quinoline, pyrrole, furan, thiophene, oxazole, pyrazole, benzodioxolane (benzodioxole), benzodioxane, benzothiophene, benzodioxepine, and thiazole, imidazole (e.g. 1-, 2- or 4-imidazole), isoxazole, isothiazole, 3-pyrazole, 1,2,3-triazole, 1,2,4-triazole, tetrazole, pyridazine, pyrazine, indazole, indole (e.g. 6-indole), benzimidazole, isoquinoline, purine, carbazole and acridine groups. A most typical heteroaryl group is pyridine.

The aforementioned aryl and heteroaryl groups may, where appropriate, optionally be substituted by one or more (e.g. 1, 2 or 3, typically 1 or 2) monovalent or multivalent functional groups. Suitable substituent groups include alkyl, cycloalkyl, phenyl, pyridyl, furyl, carbocylic, heterocyclic, alkoxy, cycloalkoxy, phenyloxy, carbocyclicoxy, hetercyclicoxy, alkenyloxy, alkynyloxy, alkenyl, alkynyl, alkanoyl, alkoxyalkanoyl, alkoxyalkyl, nitro, —S-alkyl (e.g. methylthio) halo (e.g. fluoro, chloro, bromo and iodo), cyano, hydroxyl, —SO$_2$alkyl, —SO$_2$cycloalkyl —SO$_2$heterocyclic, —CO$_2$H, —CO$_2$alkyl, —NH$_2$, —NHalkyl, —N(alkyl)$_2$ (e.g. dimethylamino), —CO—N(alkyl)$_2$ and —CO—NH(alkyl). Most typical substituent groups are selected from alkyl, alkoxy, halo, nitro and hydroxyl.

Examples of substituted aryl groups include 4-fluoro-phenyl, 3-fluoro-phenyl, pentafluoro-phenyl, 4-hydroxyphenyl-, 3-nitro-phenyl-, 4-(trifluoromethyl)-phenyl-, 4-anilinyl-, 2-biphenylyl-, 3-biphenylyl- and 4-biphenylyl-. Examples of substituted heteroaryl groups include N-methyl-2-pyrrolyl, 2-methyl-1-pyrrolyl, 3-methyl-2-pyrrolyl and 3-phenyl-1-pyrrolyl.

Examples of -alkylaryl include phenylmethyl- (i.e. benzyl) and phenylethyl, 2-phenyleth-1-yl, p-tolyl-methyl-, p-tolyl-ethyl-, m-tolyl-methyl-, m-tolyl-ethyl-, otolyl-methyl-, o-tolyl-ethyl-, 2-(4-ethyl-phenyl)-eth-1-yl-, 2,3-dimethyl-phenyl-methyl-, 2,4-dimethyl-phenyl-methyl-, 2,5-dimethyl-phenyl-methyl-, 2,6-dimethyl-phenyl-methyl-, 3,4-dimethyl-phenyl-methyl-, 3,5-dimethyl-phenyl-methyl-, 2,4,6-trimethyl-phenyl-methyl-, 2,3-dimethyl-phenyl-ethyl-, 2,4-dimethyl-phenyl-ethyl-, 2,5-dimethyl-phenyl-ethyl-, 2,6-dimethyl-phenyl-ethyl-, 3,4-dimethyl-phenyl-ethyl-, 3,5-dimethyl-phenyl-ethyl-, 2,4,6-trimethyl-phenyl-ethyl-, benzhydryl (i.e. diphenyl-methyl), diphenyl-ethyl), trityl (i.e. triphenyl-methyl), triphenyl-ethyl, cumyl (i.e. 1-methyl-1-phenylethyl), 2-ethyl-phenyl-methyl-, 3-ethyl-phenyl-methyl-, 4-ethyl-phenyl-methyl-, 2-ethyl-phenyl-ethyl-, 3-ethyl-phenyl-ethyl-, 4-ethyl-phenyl-ethyl-, 2-fluoro-benzyl, 1-methyl-2-fluoro-phen-6-yl-methyl-, 1-methyl-2-fluoro-phen-4-yl-methyl-, 1-methyl-2-fluoro-phen-6-yl-ethyl-, 1-methyl-2-fluoro-phen-4-yl-ethyl-, 1H-indenyl-methyl-, 2H-indenyl-methyl-, 1H-indenyl-ethyl-, 2H-indenyl-ethyl-, indanyl-methyl-, indan-1-on-2-yl-methyl-, indan-1-on-2-yl-ethyl-, tetralinyl-methyl-, tetralinyl-ethyl-, fluorenyl-methyl-, fluorenyl-ethyl-, dihydronaphthalinyl-methyl-, dihydronaphthalinyl-ethyl-, or (4-cyclohexyl)-phenyl-methyl-, (4-cyclohexyl)-phenyl-ethyl-. A most typical -alkylaryl group is phenylmethyl-.

Examples of -alkylheteroaryl include pyridinylmethyl- (eg 2-pyridinylmethyl), N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridino-methyl-, 4-pyridino-ethyl-, 2-(thiazol-2-yl)-ethyl-, tetrahydroisochinolinyl-methyl-, tetrahydroisochinolinyl-ethyl-, 2-ethyl-indol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl, 4-methyl-pyridin-3-ethyl. A most typical -alkylheteroaryl group is pyridinylmethyl-.

Amino Acids

Amino acids which can be used in the present invention are L and D-amino acids, N-alkylated amino acids, N-methyl-amino acids, allo- and threo-forms of Ile and Thr, which can, e.g. be α-, β- or ω-amino acids, whereof α-amino acids are preferred.

Examples of amino acids are: aspartic acid (Asp), glutamic acid (Glu), arginine (Arg), lysine (Lys), histidine (His), glycine (Gly), serine (Ser), cysteine (Cys), threonine (Thr), asparagine (Asn), glutamine (Gln), tyrosine (Tyr), alanine (Ala), proline (Pro), valine (Val), isoleucine (Ile), leucine (Leu), methionine (Met), phenylalanine (Phe), tryptophan (Trp), hydroxyproline (Hyp), beta-alanine (beta-Ala), 2-aminooctanoic acid (Aoa), acetidine-(2)-carboxylic acid (Ace), pipecolic acid (Pip), 3-aminopropionic acid, 4-aminobutyric acid and so forth, alpha-aminoisobutyric acid (Aib), sarcosine (Sar), ornithine (Orn), citrultine (Cit), homoarginine (Har), t-butylalanine (t-butyl-Ala), t-butylglycine (t-butyl-Gly), N-methylisoleucine (N-Melle), phenylglycine (Phg), cyclohexylalanine (Cha), norleucine (Nle), cysteic acid (Cya) and methionine sulfoxide (MSO), acetyl-Lys, modified amino acids such as phosphoryl-serine (Ser(P)), benzyl-serine (Ser(Bzl)) and phosphoryl-tyrosine (Tyr(P)), 2-aminobutyric acid (Abu), aminoethylcysteine (AECys), carboxymethylcysteine (Cmc), dehydroalanine (Dha), dehydroamino-2-butyric acid (Dhb), carboxyglutaminic acid (Gla), homoserine (Hse), hydroxylysine (Hyl), cis-hydroxyproline (cisHyp), trans-hydroxyproline (transHyp), isovaline (Iva), pyroglutamic acid (Pyr), norvaline (Nva), 2-aminobenzoic acid (2-Abz), 3-aminobenzoic acid (3-Abz), 4-aminobenzoic acid (4-Abz), 4-(aminomethyl)benzoic acid (Amb), 4-(aminomethyl)cyclohexanecarboxylic acid (4-Amc), Penicillamine (Pen), 2-amino-4-cyanobutyric acid (Cba), cycloalkane-carboxylic aicds. Examples of ω-amino acids are e.g.: 5-Ara (aminoraleric acid), 6-Ahx (aminohexanoic acid), 8-Aoc (aminooctanoic acid), 9-Anc (aminovanoic acid), 10-Adc (aminodecanoic acid), 11-Aun (aminoundecanoic acid), 12-Ado (aminododecanoic acid). Further amino acids are: indanylglycine (Igl), indoline-2-carboxylic acid (Idc), octahydroindole-2-carboxylic acid (Oic), diaminopropionic acid (Dpr), diaminobutyric acid (Dbu), naphtylalanine (1-Nal) and (2-Nal), 4-aminophenylalanine (Phe(4-NH$_2$)), 4-benzoylphenylalanine (Bpa), diphenylatanine (Dip), 4-bromophenylatanine (Phe(4-Br)), 2-chlorophenylalanine (Phe(2-Cl)), 3-chlorophenylalanine (Phe(3-Cl)), 4-chlorophenylalanine (Phe(4-Cl)), 3,4-chlorophenylalanine (Phe (3,4-Cl$_2$)), 3-fluorophenylalanine (Phe (3-F)), 4-fluorophenylalanine (Phe(4-F)), 3,4-fluorophenylalanine (Phe(3,4-F$_2$)), pentafluorophenylalanine (Phe(F$_5$)), 4-guanidinophenylalanine (Phe(4-guanidino)), homophenylalanine (hPhe), 3-jodophenylalanine (Phe(3-J)), 4-jodophenylalanine (Phe(4-J)), 4-methylphenylalanine (Phe(4-Me)), 4-nitrophenylalanine (Phe-4-NO$_2$)), biphenylalanine (Bip), 4-phosphonomethylphenylalanine (Pmp), cyclohexylglycine (Ghg), 3-pyridinylaianine (3-Pal), 4-pyridinylalanine (4-Pal), 3,4-dehydroproline (A-Pro), 4-ketoproline (Pro(4-keto)), thioproline (Thz), isonipecotic acid (Inp), 1,2,3,4,-tetrahydroisoquinolin-3-carboxylic acid (Tic), propargylglycine (Pra), 6-hydroxynorteucine (NU(6-OH)), homotyrosine (hTyr), 3-jodotyrosine (Tyr(3-J)), 3,5-dijodotyrosine (Tyr(3, 5-J$_2$)), methyltyrosine (Tyr(Me)), 2',6'-dimethyltyrosine (Dmt), 3-NO$_2$-tyrosine (Tyr(3-NO$_2$)), phosphotyrosine (Tyr (PO$_3$H$_2$)), alkylglycine, 1-aminoindane-1-carboxylic acid, 2-aminoindane-2-carboxylic acid (Aic), 4-amino-methylpyrrol-2-carboxylic acid (Py), 4-amino-pyrrolidine-2-carboxylic acid (Abpc), 2-aminotetraline-2-carboxylic acid (Atc), diaminoacetic acid (Gly(NH$_2$)), diaminobutyric acid (Dab), 1,3-dihydro-2H-isoinole-carboxylic acid (Disc), homocylcohexylalanine (hCha), homophenylalanine (hphe or Hof), trans-3-phenyl-azetidine-2-carboxylic acid, 4-phenyl-pyrrolidine-2-carboxylic acid, 5-phenyl-pyrrolidine-2-carboxylic acid, 3-pyridylalanine (3-Pya), 4-pyridylalanine (4-Pya), styrylalanine, tetrahydroisoquinoline-1-carboxylic acid (Tiq), 1,2,3,4-tetrahydronorharmane-3-carboxylic acid (Tpi), β-(2-thienryl)-alanine (Tha).

An "aza-amino acid" is defined as an amino acid where the chiral α-CH group is replaced by a nitrogen atom.

Other amino acid substitutions for those encoded in the genetic code can also be included in peptide compounds within the scope of the invention and can be classified within this general scheme. Proteinogenic amino acids are defined as natural protein-derived α-amino acids (e.g. the 20 common natural L-amino acids i.e.: L-Asp (aspartic acid), L-Glu (glutamic acid), L-Arg (arginine), L-Lys (lysine), L-His (histidine), Gly (glycine), L-Ser (serine), L-Cys (cysteine), L-Thr (threonine), L-Asn (asparagine), L-Gln (glutamine), L-Tyr (tyrosine), L-Ala (alanine), L-Pro (proline), L-Val (valine), L-Ile (isoleucine), L-Leu (leucine), L-Met (methionine), L-Phe (phenylalanine), L-Trp (tryptophan)). Non-proteinogenic amino acids are defined as all other amino acids, which are not building blocks of common natural proteins.

Non-cyclic amino acids include the above mentioned amino acids but excluding cyclic amino acids such as Pro and the various derivatives thereof (eg 3,4-dehydroproline (A-Pro), 4-ketoproline (Pro(4-keto)) and thioproline (Thz)). Non cyclic aza amino acids include the aza derivatives of those amino acids and excluding the cyclic aza amino acids such as the aza derivative of Pro and its various derivatives (eg the aza derivatives of 3,4-dehydroproline (A-Pro), 4-ketoproline (Pro(4-keto)) and thioproline (Thz)).

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Pharmaceutically Acceptable Salts:

In view of the close relationship between the free compounds and the compounds in the form of their salts, whenever a compound is referred to in this context, a corresponding salt is also intended, provided such is possible or appropriate under the circumstances.

The pharmaceutically acceptable salt may take a form in which a basic side chain is protonated with an inorganic or organic acid. Representative organic or inorganic acids include hydrochloric, hydrobromic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicylic, saccharinic or trifluoroacetic acid. Alternatively it may take the form in which an acidic side chain forms a salt with a metal ion (eg sodium, potassium ions and the like) or other positive ion such as ammonium. All pharmaceutically acceptable acid addition salt forms of the compounds of the present invention are intended to be embraced by the scope of this invention.

Polymorph Crystal Forms and Solvates:

Furthermore, some of the crystalline forms of the compounds may exist in more than one polymorphic form and as such all forms are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985 and the patent applications DE 198 28 113, DE 198 28 114, WO 99/67228 and WO 99/67279 which are fully incorporated herein by reference.

As used herein, the term "composition" is intended to encompass a product comprising the claimed compound(s) in the therapeutically effective amounts, as well as any product which results, directly or indirectly, from combinations of the claimed compounds.

SUMMARY OF THE INVENTION

The present invention provides compounds acting as inhibitors of prolyl endopeptidase (PEP, EC 3.4.21.26) and PEP-like enzymes. These compounds, together with their pharmaceutically acceptable salts and stereoisomers thereof, are represented by the general formula 1

W—KCONH—X—CON—Y—CO—Z     formula 1 wherein

W represents alkyl, alkenyl, alkynyl, cycloalkyl, heterocyclyl, carbocyclyl, aryl, -alkylaryl or -alkylheteroaryl;

K represents O, NH or $CH_2$;

or K is absent and W—CO represents the moiety of an amino acid or aza-amino acid;

NH—X—CO represents the moiety of non-cyclic amino acid or non-cyclic aza-amino acid, wherein when NH—X—CO represents the moiety of Asp or Glu the acid side chain of said Asp or Glu may optionally be joined via a peptide bond to another amino acid or aza-amino acid;

N—Y—CO— is selected from a moiety of formula 2a, 2b, 2c, 2d, 2e, 2f and 2g:

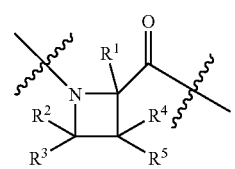

2a

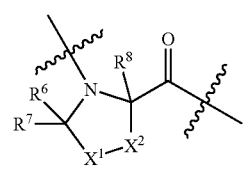

2b

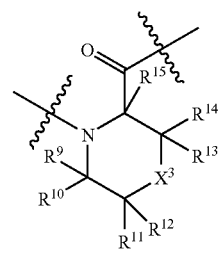

2c

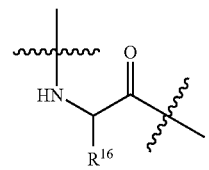

2d

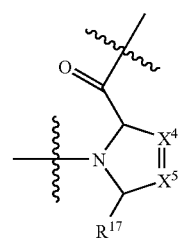

2e

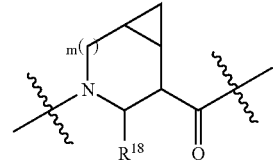

2f

-continued

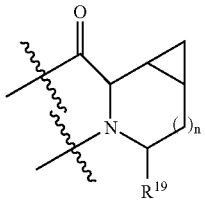

2g wherein $R^1$-$R^{15}$ and $R^{17}$-$R^{19}$ are independently H or an alkyl chain, alkenyl chain, alkynyl chain, cycloalkyl, a carbocycle, aryl, heteroaryl, heterocycle, or a group selected from halogen, amino, —$CONH_2$, CONH(alkyl), —CON(alkyl)$_2$, nitro, hydroxyl, —CN and —SCN;

or else $R^2/R^3$, $R^4/R^5$, $R^6/R^7$, $R^9/R^{10}$, $R^{11}/R^{12}$ together with the carbon atom to which they are attached independently represent oxo;

or else $R^3$ and $R^5$ are connected to form a benzene ring fused to the azetidine ring (in which case $R^2$ and $R^4$ are absent) or $R^{10}$ and $R^{11}$ are connected to form a benzene ring fused to the piperidine ring (in which case $R^9$ and $R^{12}$ are absent);

$R^{16}$ is the side chain of an amino acid moiety;

$X^1$ is $CR^{20}R^{21}$, O, S, SO, $SO_2$ or $NR^{22}$;

$X^2$ is $CR^{23}R^{24}$, O, S, SO, $SO_2$ or $NR^{25}$;

$X^3$ is $CR^{26}R^{27}$, O, S, SO, $SO_2$ or $NR^{28}$;

$R^{22}$, $R^{25}$ and $R^{28}$, independently of each other, are H, alkyl, alkenyl, alkynyl, cycloalkyl, carbocycle, heterocycle, aryl, heteroaryl, aryl-alkyl or a heteroaryl-alkyl group;

$R^{20}$, $R^{21}$, $R^{23}$, $R^{24}$, $R^{26}$ and $R^{27}$, independently of each other, are H, alkyl, alkenyl, alkynyl, cycloalkyl, carbocycle heterocycle, aryl, heteroaryl, aryl-alkyl, heteroaryl-alkyl group or, a carbaldehyde (—CHO), a ketone group (—CO—$R^{29}$), a boronic acid group (—B(OH)$_2$), a cyano group (—C≡N), a carboxylic acid group (—COOH), a carboxylic acid ester group (—COOR$^{30}$), a carboxylic acid anhydride group (—CO—O—CO—$R^{31}$), a hydroxamic acid group (—CO—NH(OH)), a N-substituted hydroxamic acid group (—CO—NR$^{32}$(OH)), a O-substituted hydroxamic acid group (—CO—NH(OR$^{33}$)), a carboxamide group (—CO—NH$_2$), a N-substituted or N,N-disubstituted carboxylic acid amide group, (—CO—NHR$^{34}$; —CO—NR$^{35}$R$^{36}$), an amido group (—HN—CO—$R^{37}$), a sulfonic acid group (—SO$_3$H), a sulfonamide group (—SO$_2$—NH$_2$), a N-substituted or N,N-disubstituted sulfonamide group (—SO$_2$—NHR$^{38}$; —SO$_2$—NR$^{39}$R$^{40}$), an amidosulfone group (—NH—SO$_2$—$R^{41}$), a sulfone group (—SO$_2$—$R^{42}$), a phosphoric acid group (—OP(=O)(OH)$_2$), a phosphoric acid ester group (—OP(=O)(OR$^{43}$)(OR$^{44}$)), a phosphonic acid group (—P(=O)(OH)$_2$), an phosphonic acid ester group (—P(=O)(OR$^{45}$)(OR$^{46}$)), a halogeno group, a trifluormethyl group (—CF$_3$), a thiol group (—SH); a thioether group (—S—$R^{47}$), a hydroxy group (—OH); an alkoxy group (—O—$R^{48}$), a tetrazole group, an amino group (—NH$_2$), or a N-substituted or N,N-disubstituted amino group (—NHR$^{49}$; —NR$^{50}$R$^{51}$); or when $X^1$ is $CR^{20}R^{21}$, $R^6$ and $R^{20}$ may be connected to form a benzene ring fused to the pyrrolidine ring (in which case $R^7$ and $R^{21}$ are absent), or when $X^2$ is $CR^{22}R^{23}$, $R^{20}$ and $R^{22}$ may be connected to form a benzene ring fused to the pyrrolidine ring (in which case $R^{21}$ and $R^{23}$ are absent); or when $X^3$ is $CR^{26}R^{27}$, $R^{11}$ and $R^{26}$ may be connected to form a benzene ring fused to the piperidine ring (in which case $R^{12}$ and $R^{27}$ are absent), or $R^{27}$ and $R^{13}$ may be connected to form a benzene ring fused to the piperidine ring (in which case $R^{26}$ and $R^{14}$ are absent);

the substituents $R^{29}$, $R^{30}$, $R^{31}$, $R^{32}$, $R^{33}$, $R^{34}$, $R^{35}$, $R^{36}$, $R^{37}$, $R^{38}$, $R^{39}$, $R^{40}$, $R^{41}$, $R^{42}$, $R^{43}$, $R^{44}$, $R^{45}$, $R^{46}$, $R^{47}$, $R^{48}$, $R^{49}$, $R^{50}$, and $R^{51}$, independently of each other are H, alkyl, alkenyl, alkynyl, cycloalkyl, carbocycle, heterocycle, aryl, heteroaryl, aryl-alkyl- or heteroaryl-alkyl-; and alternatively, the pairs $R^{35}R^{36}$, $R^{39}R^{40}$ and $R^{50}R^{51}$, independently of each other, may, together with the nitrogen to which they are attached, form a part of a heterocycle ring (eg pyrrolidine, piperidine or morpholine); or the pairs $R^{43}/R^{44}$, $R^{45}/R^{46}$ may be linked to form a $C_{1-4}$alkylene chain;

$X^4$ is $CR^{52}$ or N;

$X^5$ is $CR^{53}$ or N;

$R^{52}$ and $R^{53}$, independently of each other, are H, alkyl, alkenyl, alkynyl, cycloalkyl, carbocycle, heterocycle, aryl, heteroaryl, aryl-alkyl, heteroaryl-alkyl, aryl-heteroalkyl, heteroaryl-heteroalkyl group or, a carbaldehyde (—CHO), a ketone group (—CO—$R^{54}$), a boronic acid group (—B(OH)$_2$), a cyano group (—C≡N), a carboxylic acid group (—COOH), a carboxylic acid ester group (—COOR$^{55}$), a carboxylic acid anhydride group (—CO—O—CO—$R^{56}$), a hydroxamic acid group (—CO—NH(OH)), a N-substituted hydroxamic acid group (—CO—NR$^{57}$(OH)), a O-substituted hydroxamic acid group (—CO—NH(OR$^{58}$)), a carboxamide group (—CO—NH$_2$), a N-substituted or N,N-disubstituted carboxylic acid amide group, (—CO—NHR$^{59}$; —CO—NR$^{60}$R$^{61}$), an amido group (—HN—CO—$R^{62}$), a sulfonic acid group (—SO$_3$H), a sulfonamide group (—SO$_2$—NH$_2$), a N-substituted or N,N-disubstituted sulfonamide group (—SO$_2$—NHR$^{63}$; —SO$_2$—NR$^{64}$R$^{65}$), an amidosulfone group (—NH—SO$_2$—$R^6$), a sulfone group (—SO$_2$—$R^{67}$), a phosphoric acid group (—OP(=O)(OH)$_2$), a phosphoric acid ester group (—OP(=O)(OR$^{68}$)(OR$^{69}$)), a phosphonic acid group (—P(=O)(OH)$_2$), an phosphonic acid ester group (—P(=O)(OR$^{70}$)(OR$^{71}$)), a halogeno group, a trifluormethyl group (—CF$_3$), a thiol group (—SH); a thioether group (—S—$R^{72}$), a hydroxy group (—OH); an alkoxy group (—O—$R^{73}$), a tetrazole group, an amino group (—NH$_2$), or a N-substituted or N,N-disubstituted amino group (—NHR$^{74}$; —NR$^{75}$R$^{76}$);

the substituents $R^{54}$, $R^{55}$, $R^{56}$, $R^{57}$, $R^{58}$, $R^{59}$, $R^{60}$, $R^{61}$, $R^{62}$, $R^{63}$, $R^{64}$, $R^{65}$, $R^{66}$, $R^{67}$, $R^{68}$, $R^{69}$, $R^{70}$, $R^{71}$, $R^{72}$, $R^{73}$, $R^{74}$, $R^{75}$, and $R^{76}$, independently of each other are H or an alkyl, alkenyl, alkynyl, cycloalkyl, carbocycle, heterocycle, aryl, heteroaryl, aryl-alkyl, heteroaryl-alkyl group; and alternatively, the pair $R^{52}/R^{53}$ if present, together with the carbon atoms to which they are attached may form part of a heterocycle or carbocycle ring; or the pairs $R^{60}R^{61}$, $R^{64}R^{65}$, and $R^{75}R^{76}$, independently of each other, may, together with the nitrogen to which they are attached, form a part of a heterocycle ring (eg pyrrolidine, piperidine or morpholine); or the pairs $R^{68}/R^{69}$ and $R^{70}/R^{71}$ may be linked to form a $C_{1-4}$alkylene chain;

m represents an integer 0 to 2;

n represents an integer 0 to 2;

Z is heteroaryl, and with the proviso that the following compound:

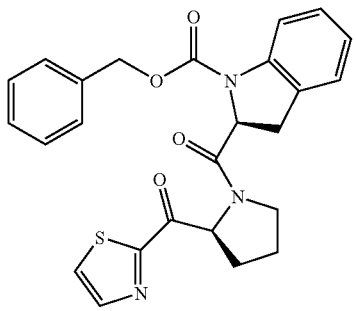

(a)

is excluded from formula 1.

The compound (a) of the proviso above is disclosed in Tsutsumi, S. et al. (1995) Acta Crystallogr. Sect. C: Cryst. Struct. Commun., 1925-1927.

BRIEF DESCRIPTIONS OF THE DRAWINGS

FIG. 1: Quantification of basal medium IL-6 in human glial U-343 cells treated with different PEP inhibitors. The conditioned medium of human glial U343 cells, treated with PEP inhibitors over 24 hours contained only 15% to 60% of IL-6 amount measured in untreated control samples. Values are presented as mean±SD of quadruplicate wells and were analyzed for statistical significance by unpaired t test (***$p<0.001$).

Figure 2:
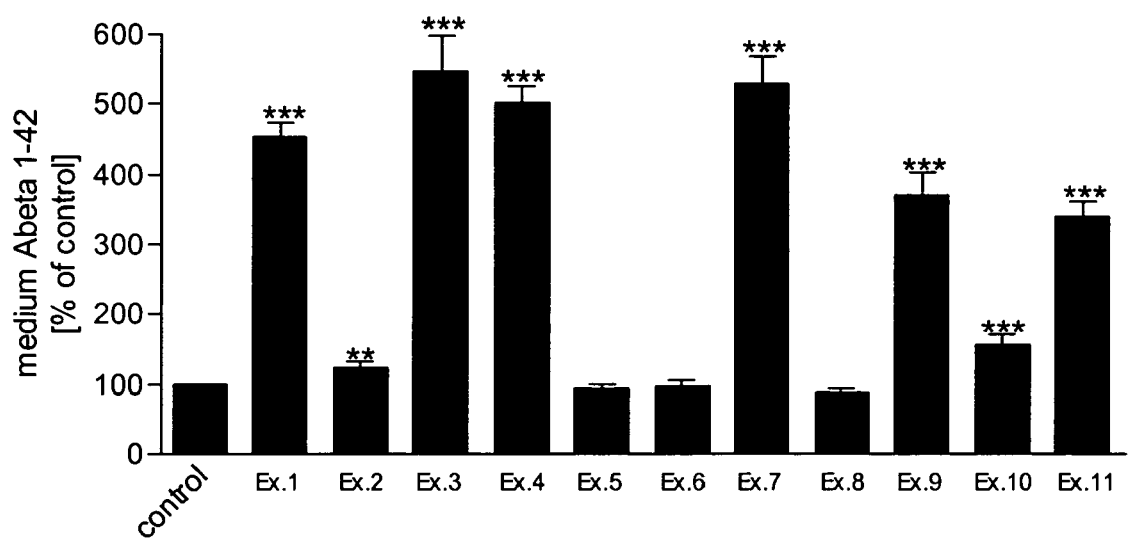

FIG. 2: Quantification of basal Aβ 1-42 value in human neuroblastoma SH-SY5Y cells treated with different PEP inhibitors. The conditioned medium of human glial U343 cells, treated with PEP inhibitors over 24 hours contained 87.5% to 546% of Aβ 1-42 amount measured in untreated control samples. Values are presented as mean±SD of quadruplicate wells and were analyzed for statistical significance by unpaired t test (***$p<0.001$).

Figure 3A:
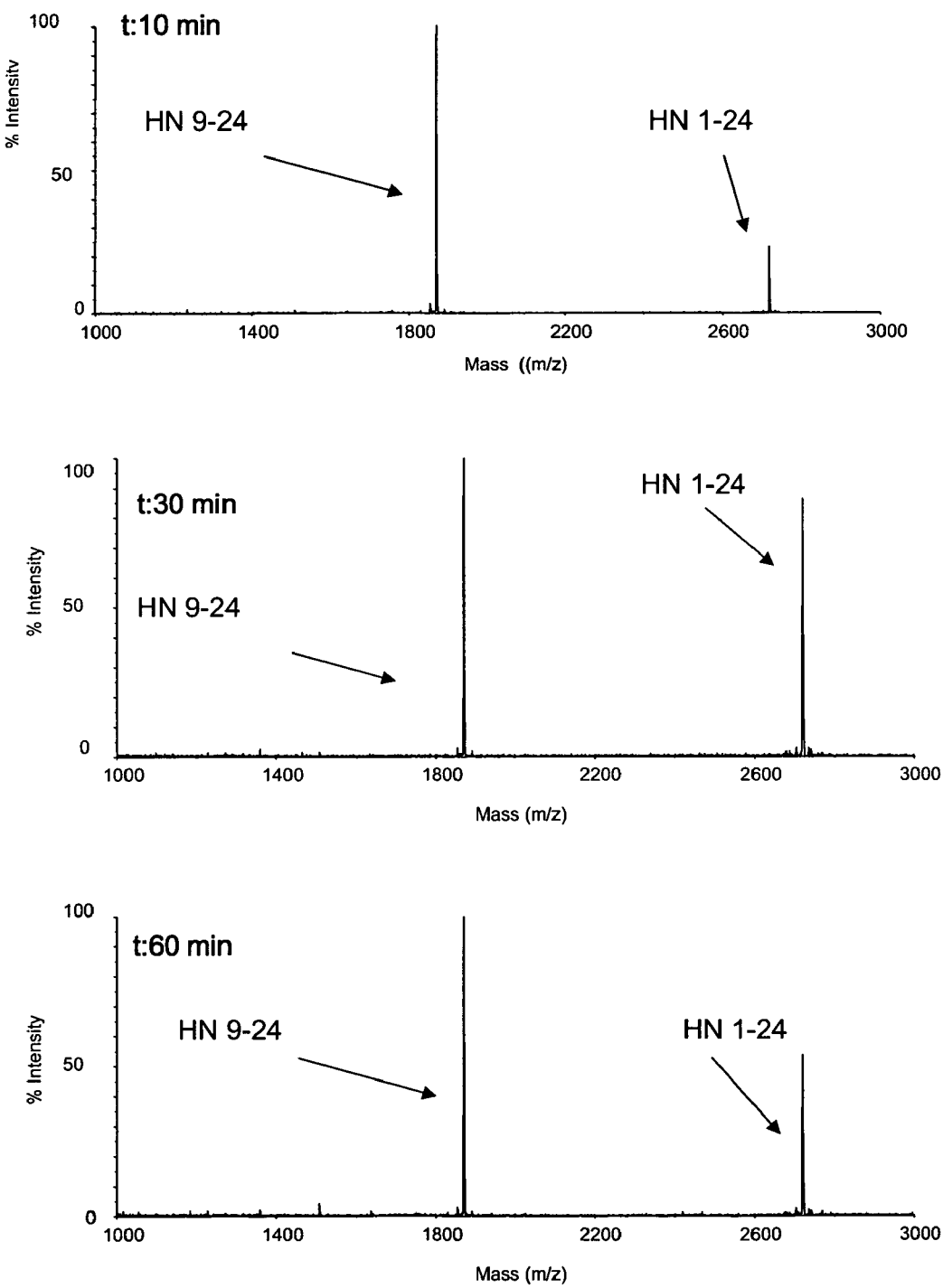
Figure 3B:
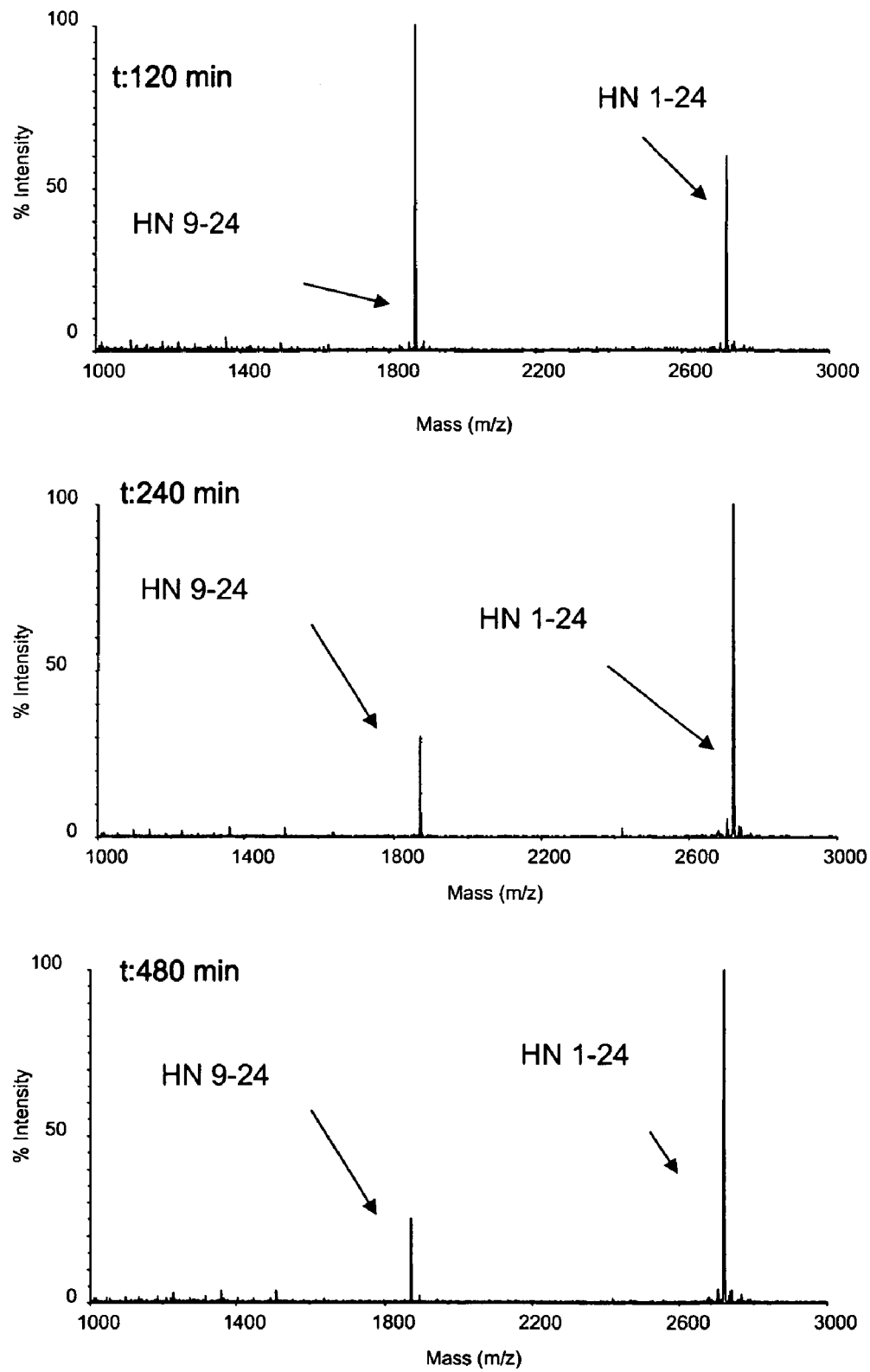
Figure 3C:
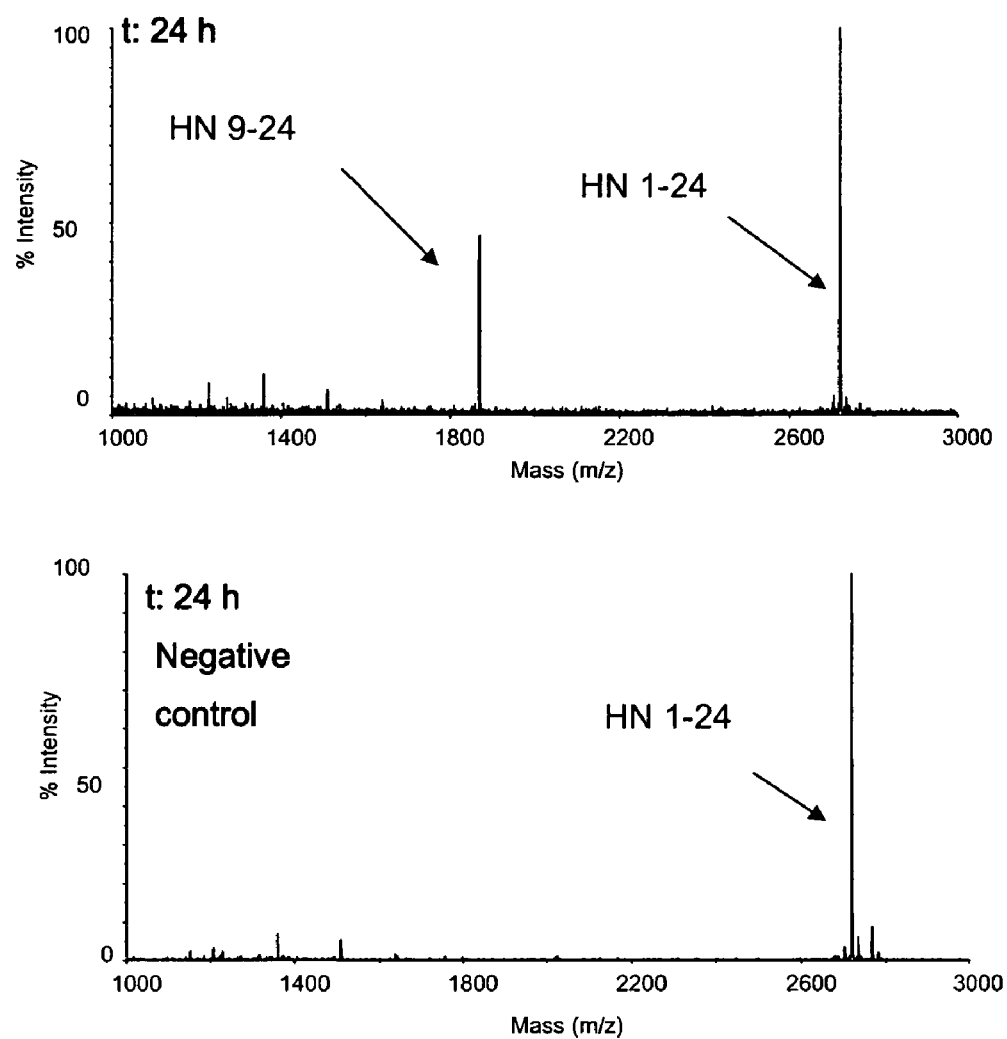

FIG. 3: PEP catalysed degradation of humanin—positive control without inhibitor. The cleavage products are determined by matrix-assisted laser desorption mass spectrometry. HN 1-24 represents full length humanin. HN 9-24 represents post cysteine cleaved humanin 9-24.

Figure 4A:
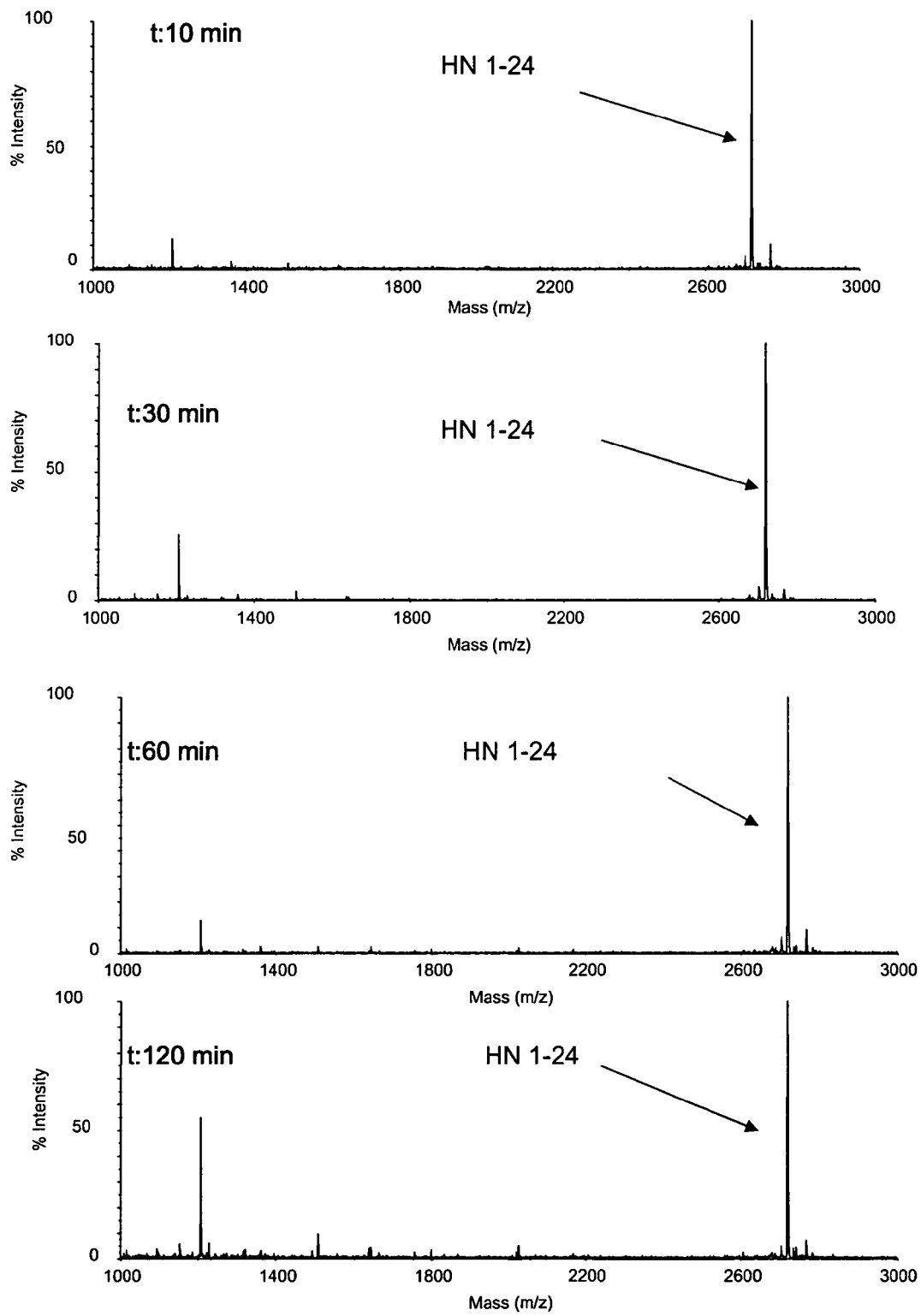
Figure 4B:
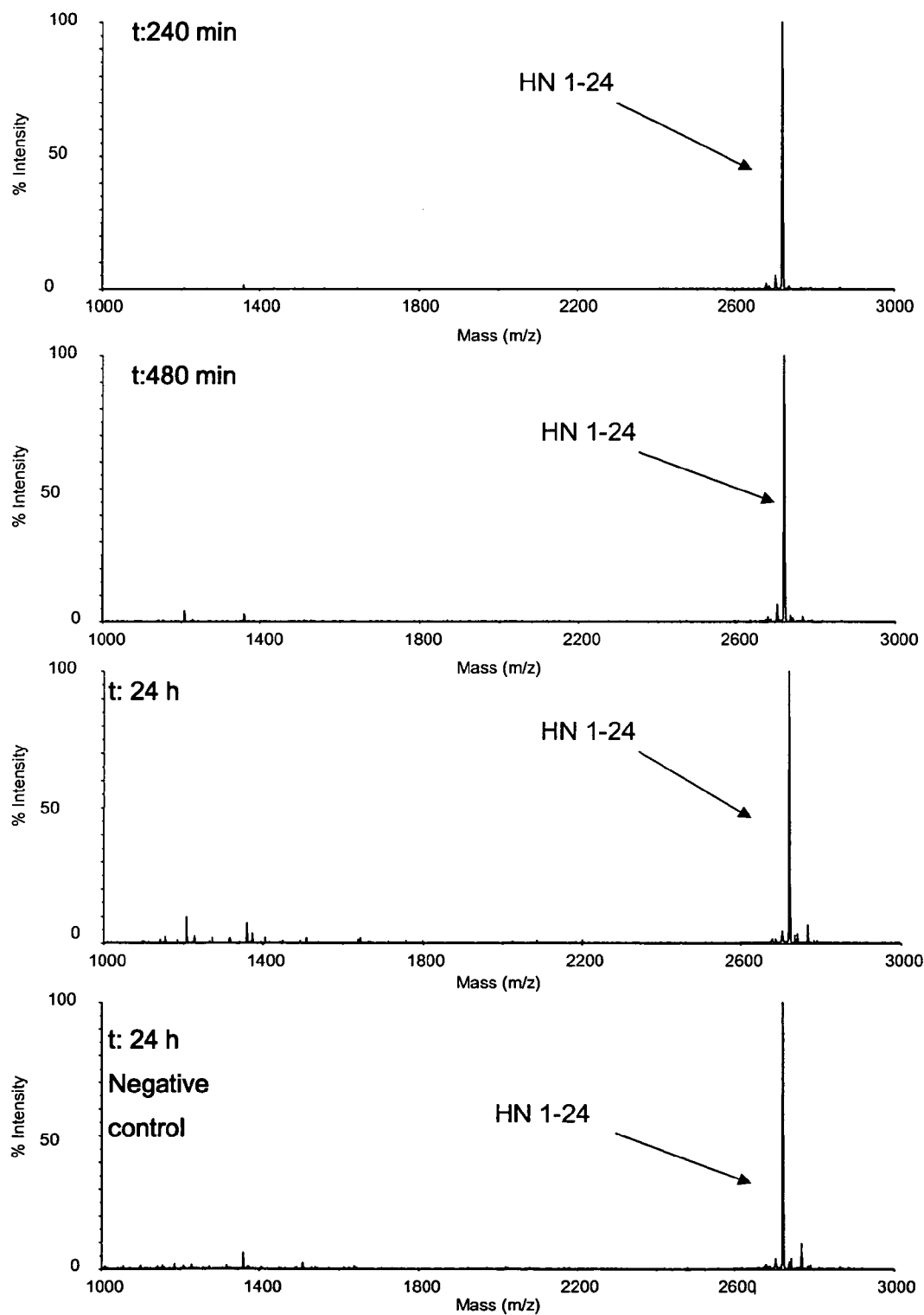

FIG. 4: PEP catalysed degradation of humanin—PEP inhibitor Example 2 present. The cleavage products are determined by matrix-assisted laser desorption mass spectrometry. HN 1-24 represents full length humanin. HN 9-24 represents post cysteine cleaved humanin 9-24.

Figure 5A:
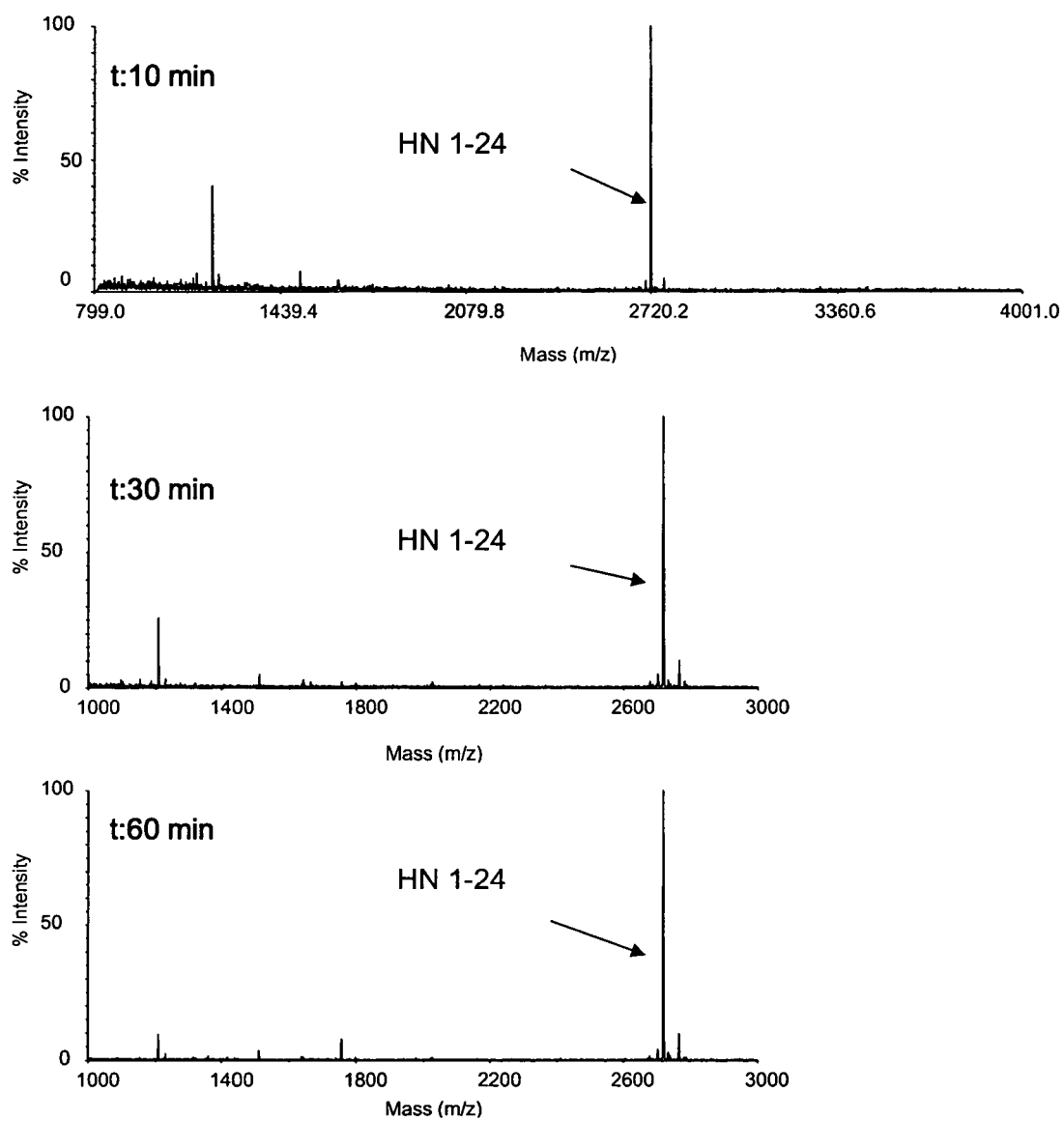
Figure 5B:
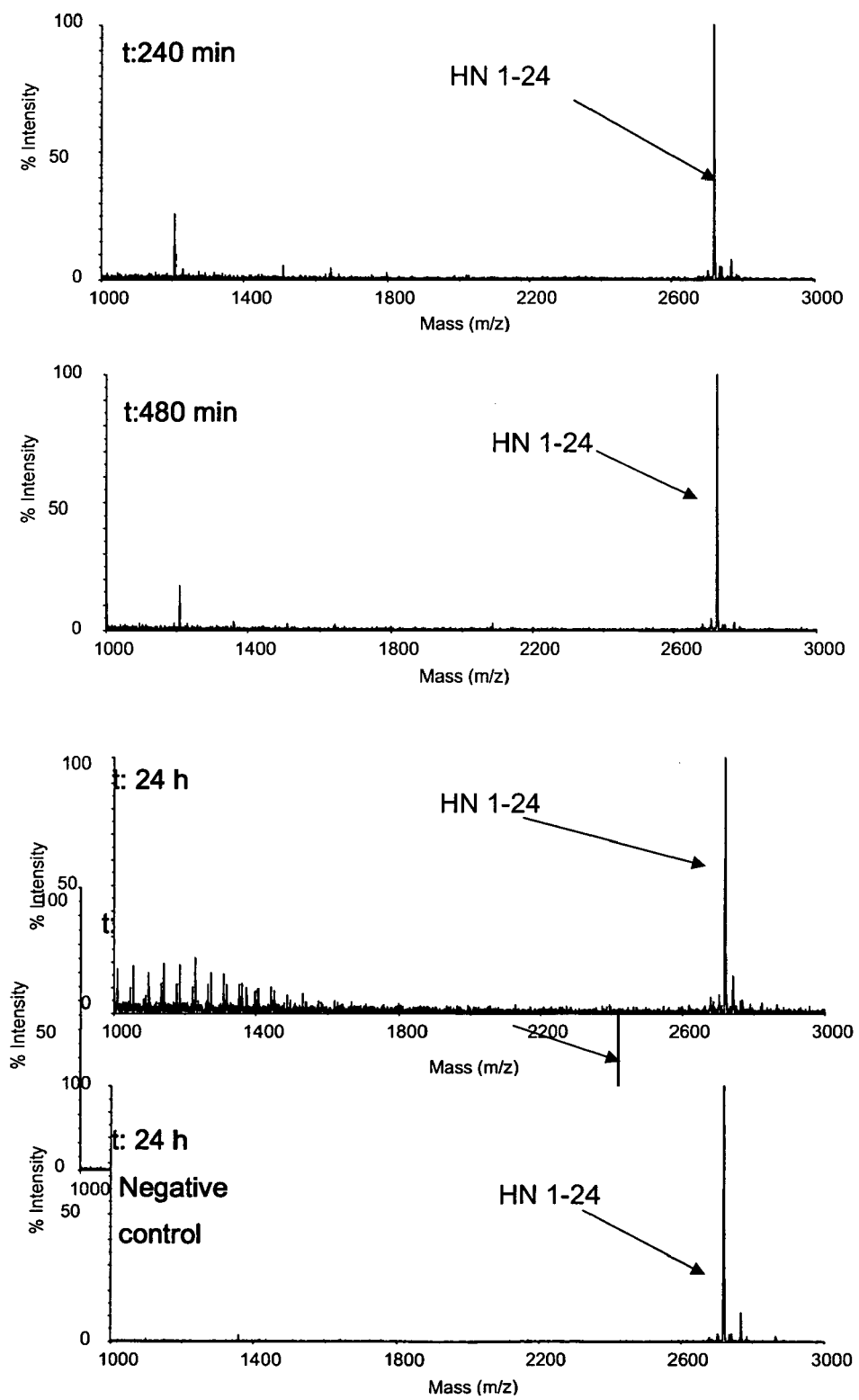

FIG. 5: PEP catalysed degradation of humanin—PEP inhibitor Example 2 present. The cleavage products are determined by matrix-assisted laser desorption mass spectrometry. HN 1-24 represents full length humanin. HN 9-24 represents post cysteine cleaved humanin 9-24.

DETAILED DESCRIPTION OF THE INVENTION

Preferably W represents -alkylaryl (eg -methylaryl), -alkylheteroaryl (eg methylheteroaryl), alkyl, alkenyl, alkynyl or cycloalkyl. More preferably W represents alkenyl-(eg $C_{2-6}$alkenyl), alkyl-(eg $C_{2-6}$ alkyl) or arylalkyl- (eg arylmethyl-), especially arylalkyl- (eg arylmethyl). In group W aryl may for example represent phenyl optionally substituted by alkyl and/or halo. In group W heteroaryl may for example represent pyridyl optionally substituted by alkyl and/or halo. When K is absent and W—CO represents the moiety of an amino acid or aza amino acid, W—CO may for example represent the moiety of L-Phe (i.e W is —CH(NH$_2$)(CH$_2$Ph) or L-Tyr (i.e. W is —CH(NH$_2$)(CH$_2$PhOH)

Preferably K represents O or CH$_2$, especially O.

Most preferably W—K—CO represents allyloxycarbonyl (Aloc), t-butyloxycarbonyl (Boc) or benzyloxycarbonyl (Cbz), particularly benzyloxycarbonyl.

Preferably NH—X—CO represents the moiety of a non-cyclic amino acid, more preferably a proteinogenic amino acid, most preferably L-Ala (i.e. X is CH(Me)), L-Arg (i.e. X is CH(CH$_2$CH$_2$CH$_2$NHC(=NH$_2$)NH$_2$), L-Asp (i.e. X is CH(CH$_2$COOH) or L-Phe (i.e. X is CH$_2$Ph), particularly L-Ala, L-Arg or L-Phe. A further example is L-Lys (i.e. X is (CH$_2$)$_4$NH$_2$).

Typically $R^{16}$ will represent the sidechain of a proteinogenic amino acid. Examples of group $R^{16}$ include H, methyl, —CH$_2$OH, —CH(Me)OH, CHMe$_2$, CH$_2$CHMe$_2$, CH(Me)CH$_2$Me, CH$_2$CH$_2$CONH$_2$, —CH$_2$COOH, —CH$_2$CONH$_2$ and CH$_2$CH$_2$COOH.

In one embodiment of the invention N—Y—CO represents a moiety of formula 2a, 2e, 2f or 2g. In another embodiment of the invention N—Y—CO represents a moiety of formula 2b or 2c. In another embodiment of the invention N—Y—CO represents a moiety of formula 2d, especially wherein $R^{16}$ represents alkyl eg methyl (i.e. the moiety of Ala, especially L-Ala).

Preferably N—Y—CO represents a moiety of formula of 2h or 2i:

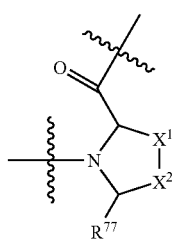

2h

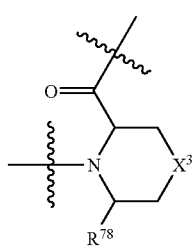

2i wherein $X^1$, $X^2$ and $X^3$ are as defined above; and $R^{77}$ and $R^{78}$ independently represent H, halogen, CN or alkyl eg H, CN or Me. $R^{77}$ and $R^{78}$ may for example independently represent CN. Alternatively they may independently represent Me. Preferably they independently represent H.

More preferably N—Y—CO represents a moiety of formula 2j or 2k:

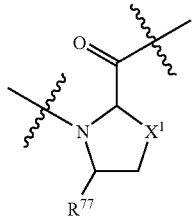

2j

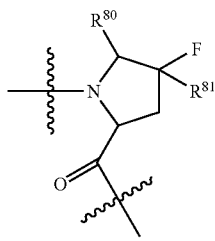

2k wherein R$^{77}$ and X$^{1}$ are as defined above and R$^{80}$ and R$^{81}$ are independently H or fluoro.

Most preferably, N—Y—CO represents L-Pro in which the pyrrolidine ring is optionally substituted by methyl, eg a moiety of formula 2j in which R$^{77}$ represents H or methyl and X$^{1}$ represents CH$_2$, especially unsubstituted L-Pro.

Preferably R$^{1}$-R$^{15}$ and R$^{17}$-R$^{19}$ independently represent H, halogen (eg F), CN or alkyl (eg Me) eg H, CN or Me, especially H.

Most preferably, R$^{1}$, R$^{2}$, R$^{3}$, R$^{4}$, R$^{5}$, R$^{6}$, R$^{7}$, R$^{8}$, R$^{9}$, R$^{10}$, R$^{11}$, R$^{12}$, R$^{13}$, R$^{14}$, R$^{15}$, R$^{17}$, R$^{18}$ and R$^{19}$ are halogen (eg F) or H, especially H.

Preferably, R$^{20}$, R$^{21}$, R$^{23}$, R$^{24}$, R$^{26}$, R$^{27}$, R$^{28}$, R$^{52}$ and R$^{53}$ are H.

Preferably groups R$^{29}$-R$^{51}$ represent H.
Preferably groups R$^{54}$-R$^{76}$ represent H.
Preferably X$^{1}$ represents CH$_2$ or CHMe, particularly CH$_2$.
Preferably X$^{2}$ represents CH$_2$ or CHMe, particularly CH$_2$.
Preferably X$^{3}$ represents CH$_2$ or CHMe, particularly CH$_2$.
Preferably X$^{4}$ represents CH or CMe, particularly CH.
Preferably X$^{5}$ represents CH or CMe, particularly CH.
Preferably n represents 0 or 1, particularly 0.
Preferably m represents 0 or 1, particularly 0.
Preferably Z represents a 5-membered heteroaryl ring optionally fused to a benzene ring (especially when linked to the remainder of the molecule through the 5-membered heteroaryl ring) more preferably 2-furan, 2-imidazole, 2-thiazole, 4-thiazole, 5-thiazole, 2-thiophene, 3-thiophene, 2-oxazole, 4-oxazole, 5-oxazole, 2-pyrrole, 3-pyrrole, 2-benzo[d]imidazole, 2-benzo[d]thiazole, 2-benzo[b]thiophene, 3-benzo[b]thiophene, 2-benzo[d]oxazole, 2-indole, 3-indole, or is selected from a moiety of formula 3a, 3b, 3c, 3d or 3e:

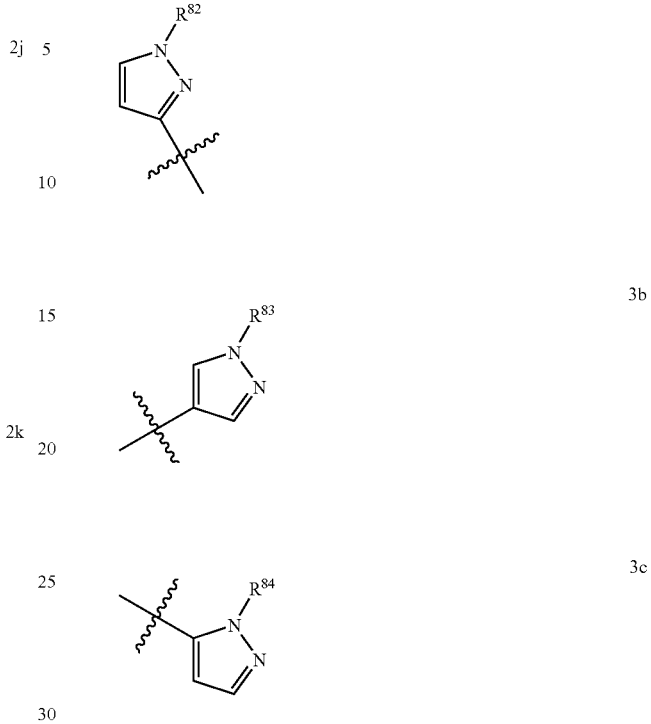

wherein R$^{82}$, R$^{83}$, R$^{84}$, R$^{85}$ and R$^{86}$ are independently H or an alkyl chain, alkenyl chain, alkynyl chain, cycloalkyl, a carbocycle, aryl, heteroaryl, heterocycle, or a group selected from halogen, amino, —CONH$_2$, CONH(alkyl), —CON(alkyl)$_2$, nitro, hydroxyl, oxo, —CN and —SCN.

Groups R$^{82}$, R$^{83}$, R$^{84}$, R$^{85}$ and R$^{86}$ are typically H or alkyl (eg methyl), more typically H.

Z more preferably is 2-imidazole, 2-thiazole, 4-thiazole, 5-thiazole, 2-thiophene, 3-thiophene, 2-oxazole, 4-oxazole, 5-oxazole, 3-pyrazole, 4-pyrazole, 5-pyrazole, 2-pyrrole, 3-pyrrole, 3-triazole, 2-benzo[d]imidazole, 2-benzo[d]thiazole, 2-benzo[b]thiophene, 3-benzo[b]thiophene, 2-benzo[d]oxazole, 2-indole or 3-indole, especially 2-thiazole or 2-benzo[d]thiazole. Another group of particular interest is pyrrole eg 2-pyrrole.

According to one particular embodiment of the invention we provide a compound of formula (I) with the proviso that the following compound:

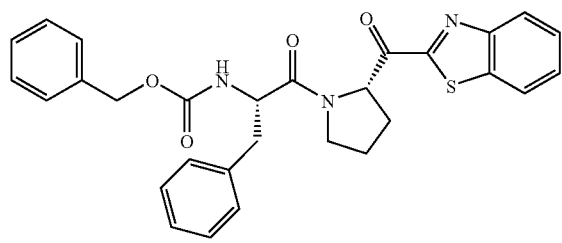

is also excluded from formula (1).

This compound is disclosed in US2005/0171112.

The PEP-inhibitors of the present invention are shown to be surprisingly effective to modulate the basal level of interleukin-6 (IL-6) in human glial cells. These compounds show a significant suppression of IL-6 secretion. This is not known for any PEP-inhibitor described in the prior art.

IL-6, a pleiotropic cytokine, contributes to a multitude of neuropathological and pathophysiological processes, especially in inflammation, cancer, infection and autoimmune diseases. Overexpression of IL-6 has been implicated in the pathology of multiple myeloma, solid tumors, prostatic cancers, bladder cancers, neurological cancers, Castleman's disease, inflammation, myocardial infarction, Paget's disease, ischemia, asthma, rheumatoid arthritis, psoriasis, Alzheimer's disease, multiple sclerosis, meningitis, stroke, osteoporosis, insulin resistance, obesity, impaired glucose tolerance, type 2 diabetes, cancer-related anorexia and cachexia as well as multidrug resistance. Therefore, reduction of pathological IL-6 concentrations by compounds which are described here may be useful in treatment of IL-6 related diseases, for instance those mentioned above.

Furthermore, the PEP-inhibitors of the present invention are shown to be surprisingly effective at modulating the basal level of β-amyloid peptides, especially of $A\beta_{1-40}$ and $A\beta_{1-42}$ in different human cell lines, e.g. neuronal cells. The compounds of the present invention show a significant increase of the secretion of β-amyloid peptides. This is not known for any PEP-inhibitor described in the prior art.

β-amyloid peptides are considered to be the cause of neurodegeneration and neuronal cell death in patients faced with MCI (Mild Cognitive Impairment) Alzheimer's disease (AD) and for the progression of MCI to AD. Recently, it was shown that the β-amyloid species, which are involved in the onset of MCI and AD, are formed intracellularly. Moreover, not the full-length peptides $A\beta_{1-40}$ and $A\beta_{1-42}$ but N-terminally truncated and N-terminally modified forms of β-amyloid peptides, e.g. $A\beta_{3-40}$, $A\beta_{3-42}$, pGlu-$A\beta_{3-40}$, pGlu-$A\beta_{3-42}$, $A\beta_{11-42}$ and pGlu-$A\beta_{11-42}$ are discussed as the toxic forms (Piccini et al., J. Biol. Chem. 280 (40), 2005, pp. 34186-34192).

The compounds of the present invention should therefore be useful to prevent the formation of neurotoxic β-amyloid peptides, e.g. $A\beta_{3-40}$, $A\beta_{3-42}$, pGlu-$A\beta_{3-40}$, pGlu-$A\beta_{3-42}$, $A\beta_{11-42}$ and pGlu-$A\beta_{11-42}$ by enhancement of the secretion of full-length $A\beta_{1-40}$ and $A\beta_{1-42}$ before N-terminal truncation and modification.

The Inventors have demonstrated for the first time that a protease is able to cleave a substrate after a cysteine residue in the peptide chain. Furthermore, we have demonstrated that the peptide humanin is a substrate for PEP. Specifically, we have demonstrated that prolyl endopeptidase is able to cleave the peptide humanin at two positions in the peptide sequence, after the proline residue in position 3 and after the cysteine residue at position 8. This cleavage pattern can be completely inhibited by the use of specific PEP inhibitors.

Humanin was originally discovered by means of a unbiased functional screening for genes suppressing FAD (familial Alzheimer's disease) and Aβ induced neuronal cell death, respectively [30, 32]. The peptide is an unusually 75 bp gene product of the mitochondrial 16S ribosomal RNA [27,30]. The evidence for a cellular expression of this gene product was given by Western blots using a peptide-antibody [33]. A detailed analysis of the physiological activity revealed the existence of a humanin core domain (residues 3 to 19) [34, 35]. In particular conservation of seven residues like Pro(3); Cys(8); Leu(9); Leu(12); Thr(13); Ser(14) and Pro(19) turned out to be essential [34,35]. Replacement of these residues by alanine or abbreviation of the core sequence results in a loss of the apoptosis rescue ability of humanin.

Humanin was recently highlighted for its ability to suppress apoptosis by interacting with the Bcl2-associated X protein (Bax) [27]. An additional interaction with the insulin-like growth factor binding protein-3 (IGFBP-3), thereby blocking the IGFBP-3 induced cell death in glioblastoma cells, supports humanin's cell survival promoting capacity [28]. The 24 amino acid peptide is able to preserve cortical neurons from prion-peptide-or amyloid-β induced insults [29,39], improves impaired metabolic activity and prolongs survival of serum-deprived human lymphocytes [31].

Accordingly, PEP-inhibitors are useful for the prevention of the degradation of peptide substrates, which can be degraded by post cysteine cleavage, e.g. the peptide humanin. Furthermore, the present invention provides a method for the prevention of the degradation of peptide substrates, which can be degraded by post cysteine cleavage, e.g. the peptide humanin. The compounds of formula (I) are especially suitable for use in this method.

The compounds of the present invention have several unique and surprising properties and are expected to be useful for the treatment of neurodegenerative diseases, e.g. MCI, AD, Down Syndrome, Parkinson disease and Chorea Huntington.

Methods for preparing compounds of formula 1 are set out in Scheme 1 and elaborated in Scheme 2, Scheme 3 and Scheme 4 and the General Methods. Thus, referring to Scheme 1 route I, a process for preparing compounds of formula 1 comprises reacting a compound of formula A with a compound of formula B under conditions of metallation. Dipeptides of formula A are activated molecules (Weinrebamides), which may be reacted with a organometallic (eg organolithium) derivatives of compounds of formula B. Dipeptides of formula A may be prepared by reacting a dipeptide of formula C (usually activated eg as a mixed anhydride) with a compound of formula D (Weinreb activating group). Compounds of formula C (dipeptides with free C-terminus) may be prepared by hydrolysing a compound of formula E (ester). Compounds of formula E may be prepared by reacting a compound of formula F (N-protected amino acid derivative) (typically activated eg as the mixed anhydride) with a compound of formula G (C-protected amino acid derivative). Alternatively, referring to Scheme 1 route II, a process for preparing compounds of formula 1 comprises oxidising a precursor compound characterised as alcohol of formula H. Compounds of formula H are accessible from compounds of formula J (Z-component with free N-terminus) via a coupling reaction. Compounds of formula J are typically obtained by deprotection of protected derivatives of formula K. Compounds of formula K (N-protected Z-component) are accessible starting from compounds of formula L via reduction to alcohol (formula La) and subsequent oxidation to the corresponding aldehyde (formula Lb). This aldehyde compound may then be reacted with organolithium derivative of component Z (eg a compound of formula B). Finally, referring to Scheme 1 route 3, a process for preparing compounds of formula 1 comprises the arylation by a Grignard reagent of formula Q reacting with a compound of formula E. The compound of formula Q may be readily prepared from the aryl compound H—Z and Grignard reagent MeMgBr which is available on the market.

Compounds of formula (1) may also be prepared by deprotecting a protected compound of formula (1).

Hence as an aspect of the invention we provide a process for preparing a compound of formula (1) which comprises:

(a) reacting a compound of formula A:

W—KCONH—X—CON—Y—COR$^x$ (A)

wherein W, K, X and Y are as defined above and R$^x$ represents a Weinreb activating group;

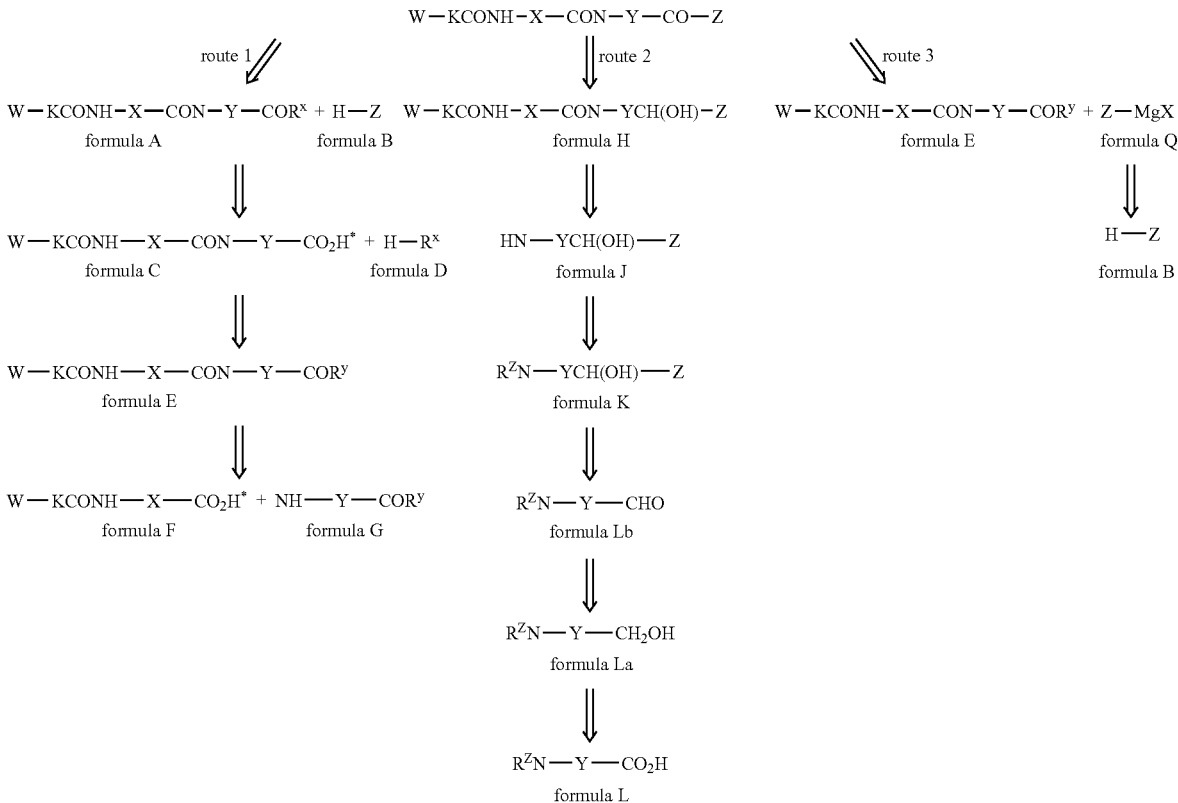

Scheme 1. Retrosynthesis of compounds comprising formula 1. R$^x$=Weinreb activating group i.e. N(CH$_3$)OCH$_3$, R$^y$=alkoxy such as OMe, R$^Z$=an amine protecting group such as Boc. *indicated that group may suitable be activated eg as a mixed anhydride. Compounds of formulas B, D, G and L are available on the market or may be prepared by known methods.

In Scheme 1, compounds of formula G and L may be readily prepared from compounds of formula HN—Y—COOH (formula M).

Specific synthetic routes and synthetic schemes for the starting materials for compounds of formula M are well known in the art. For example references which disclose synthesis routes and synthesis schemes of these compounds (or close analogue) when Y is 2a, 2c, 2e, 2f, 2g, 2h, 2i, 2j are listed in Table 1. These references are incorporated herein in their entirety and are part of the present invention with regard to the synthesis of the compounds of formula M when Y is 2a, 2c, 2e, 2f, 2g, 2h, 2i, 2j and 2k.

Other compounds of formula M and compounds of formula B, D and F are known or may be prepared by conventional methods known per se.

or a protected derivative thereof,
with a compound of formula B:

H—Z (B)

wherein Z is as defined above
or a protected derivative thereof; or
(b) oxidizing a compound of formula H:

W—KCONH—X—CON—Y—CH(OH)—Z (H)

wherein W, K, X, Y and Z are as defined above
or a protected derivative thereof;
and if necessary deprotecting the resultant product to obtain a compound of formula (1).

As an alternative route to compounds of formula (I), intermediate compounds of formula E may be converted directly to a compound of formula (I) by arylation with a Grignard reagent (see Scheme 4).

Thus as a further aspect of the invention we also provide a process for preparing a compound of formula (1) which comprises:

(c) reacting a compound of formula E:

W—KCONH—X—CON—Y—COR$^y$ (E)

wherein W, K, X and Y are as defined above and R$^y$ represents an alkoxy group eg OC$_{1-4}$alkyl such as OMe;
or a protected derivative thereof,
with a compound of formula Q:

$$Z—MgX \quad (Q)$$

wherein Z is as defined above and X represents halogen eg Br;
followed by work-up with water or an aqueous buffer.

Compounds of formula Q may be prepared by reacting the heteroaryl compound Z with a suitable alkyl magnesium halide compound such as MeMgBr.

Suitable conditions for the reaction with the Grignard reagent (Q) will be known to a person skilled in the art.

TABLE 1

References disclosing the synthetic routes and synthesis schemes of compounds of formula M (or close analogue) when Y represents formula 2a, 2c, 2e, 2f, 2g, 2h, 2i, 2j and 2k

| Reference for synthetic route and synthesis schemes | Compound of formula M |
|---|---|
| WO 04/007446A1, pp. 12-16, International Publication Date: Jan. 22, 2004 | 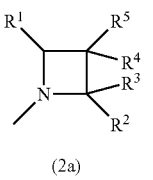 (2a) |
| WO 01/34594 A1, pp. 48-49, International Publication Date: May 17, 2001; | (2c) |
| WO 03/000181A2, pp. 25-32, International Publication Date: Jan. 3, 2003 | 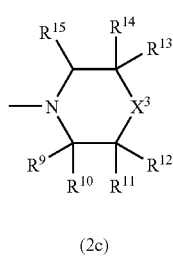 (2j) |
| WO 01/55105 A1, pp. 17-18, International Publication Date: Aug. 2, 2001 | 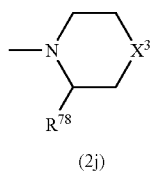 (2e) |
| WO 01/68603A2, pp. 8-11, International Publication Date: Sep. 20, 2001 | 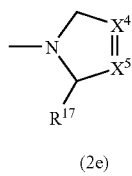 (2f) or (2g) |

TABLE 1-continued

References disclosing the synthetic routes and synthesis schemes of compounds of formula M (or close analogue) when Y represents formula 2a, 2c, 2e, 2f, 2g, 2h, 2i, 2j and 2k

| Reference for synthetic route and synthesis schemes | Compound of formula M |
|---|---|
| WO 01/34594 A1, pp. 21-22, International Publication Date: May 17, 2001 | (2h) |
| WO 03/000180A2, pp. 26-35, International Publication Date: Jan. 3, 2003; | (2j) |
| WO 04/026822A2, pp. 32-40, International Publication Date: Apr. 1, 2004 | |
| WO 03/00250A1, pp. 11—14, International Publication Date: Jan. 3, 2003 | 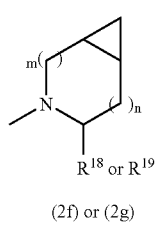 (2k) |

The present invention provides the compounds of formula 1 for use as a medicament.

The compounds of formula 1 are inhibitors of PEP and PEP-like enzymes.

Furthermore, the present invention provides the use of inhibitors of PEP and PEP-like enzymes of the formula 1 for the preparation of a medicament for the treatment of a disease selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoffs syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders.

The present invention also provides inhibitors of PEP and PEP-like enzymes of the formula 1 for use in the treatment of a disease selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoffs syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders, The present invention also provides a method of treatment for a disease selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormonal balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders, comprising the administration of a therapeutically active amount of at least one compound of formula 1 to a mammal, preferably a human.

Most preferably, the present invention provides a method of treatment and corresponding uses for a disease selected from the group consisting of mild cognitive impairment (MCI), Alzheimer's disease, Down Syndrome, Parkinson disease and Chorea Huntington, comprising the administration of a therapeutically active amount of at least one compound of formula 1 to a mammal, preferably a human.

In a further embodiment, the compounds of formula I are useful to inhibit microbial growth, reduce perioperative blood loss, preserve transplantation tissues or organs, inhibit cancer cell growth or tumor progression or tumor metastasis or invasion.

Combinations

In a further embodiment, the present invention provides a composition, preferably a pharmaceutical composition comprising at least one compound of formula 1 optionally in combination with at least one compound selected from the group consisting of inhibitors of glutaminyl cyclase (QC), LiCl, inhibitors of dipeptidyl aminopeptidases, preferably inhibitors of DP IV or DP IV-like enzymes, NPY-receptor ligands, NPY agonists, acetylcholinesterase (AChE) inhibitors, protein isoaspartate carboxymethyl transferase (PIMT) enhancers, inhibitors of beta secretases, inhibitors of gamma secretases, inhibitors of neutral endopeptidase, inhibitors of Phosphodiesterase-4 (PDE-4), monoamine oxidase (MAO) inhibitors, TNFalpha inhibitors, amyloid protein or amyloid peptide deposition inhibitors, sigma-1 receptor inhibitors and histamine H3 antagonists.

These combinations provide a particularly beneficial effect on behavioral conditions and such combinations are therefore shown to be effective and useful for the treatment of a disease selected from the group consisting of Alzheimer's disease, Down Syndrome, Parkinson disease, Chorea Huntington, pathogenic psychotic conditions, schizophrenia, impaired food intake, sleep-wakefulness, impaired homeostatic regulation of energy metabolism, impaired autonomic function, impaired hormorial balance, impaired regulation, body fluids, hypertension, fever, sleep dysregulation, anorexia, anxiety related disorders including depression, seizures including epilepsy, drug withdrawal and alcoholism, neurodegenerative disorders including cognitive dysfunction, dementia, aphasia, apraxia, agnosia, or any type of amnesias, mild cognitive impairment (MCI), benign forgetfulness and Korsakoff's syndrome, pulmonary vascular disease, restenosis or pulmonary hypertension myocarditis, bronchopulmonary dysplasia, myocardial necrosis or post-cardiac transplant coronary arteriopathy, atherosclerosis, reperfusion injury, hypoxia, ischemia and blood coagulation disorders.

The combinations of the present invention are further useful to inhibit microbial growth, reduce perioperative blood loss, preserve transplantation tissues or organs, inhibit cancer cell growth or tumor progression or tumor metastasis or invasion.

Pharmaceutical Compositions

The invention provides pharmaceutical compositions containing at least one compound of formula 1 optionally in combination with at least one agent as mentioned for the combinations above, together with one or more therapeutically acceptable diluents or carriers. The active ingredient(s) is intimately admixed with a pharmaceutical diluent or carrier according to conventional pharmaceutical compounding techniques, which diluent or carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenteral administration, the carrier will usually comprise sterile water, though other ingredients, for example, for purposes such as aiding solubility or for preservation, may be included.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

Where the processes for the preparation of the compounds of the present invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also resolved by formation of diastereomeric esters or amides, followed by chromatographic separation and removal of the chiral auxiliary. Alternatively, the compounds may be resolved using a chiral HPLC column.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyl eneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Preferably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

Suitably, in the case of combinations according to the invention, the particularly beneficial effect provided by the treatment of the invention is an improved therapeutic ratio for the combination of the invention relative to the therapeutic ratio for one compound of the combination when used alone and at a dose providing an equivalent efficacy to the combination of the invention.

In a preferred aspect, the particularly beneficial effect provided by the treatment of the invention is indicated to be a synergistic effect relative to the control expected from the effects of the individual active agents.

In a further aspect of the invention, combining doses of at least one compound of formula 1 with at least one agent as defined for the combinations herein will preferably produce a greater beneficial effect than can be achieved for either agent alone at a dose twice that used for that agent in the combination.

In a preferred aspect, the dosage level of each of the active agents when used in accordance with the treatment of the invention will be less than would have been required from a purely additive effect upon the neuronal condition.

Without being limited by theory, it is also considered that the treatment of the invention will effect an improvement, relative to the individual agents, in decreasing the intracellular deposition of pGlu-amyloid-beta-peptides and thereby dramatically slowing down the plaque formation in the brain of a mammal, preferably in human brain.

In a further aspect, the invention also provides a process for preparing a pharmaceutical composition comprising at least one at least one compound of formula 1 optionally in combination with at least one agent as defined for the combinations herein and a pharmaceutically acceptable carrier therefor, which process comprises admixing the compound of formula 1 and said optional agent(s) and a pharmaceutically acceptable diluent or carrier.

The compositions are preferably in a unit dosage form in an amount appropriate for the relevant daily dosage.

Suitable dosages, including especially unit dosages, of the compounds of formula 1, QC-inhibitors, LiCl, inhibitors of dipeptidyl aminopeptidases, preferably inhibitors of DP IV or DP IV-like enzymes, NPY-receptor ligands, NPY agonists, acetylcholinesterase (AChE) inhibitors, PIMT enhancers, inhibitors of beta secretases, inhibitors of gamma secretases, inhibitors of neutral endopeptidase, inhibitors of Phosphodiesterase-4 (PDE-4), monoamine oxidase (MAO) inhibitors, TNFalpha inhibitors, amyloid protein or amyloid peptide deposition inhibitors, sigma-1 receptor inhibitors and histamine H3 antagonists include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

Preferred compounds of formula 1 are those having an $IC_{50}$ value or a $K_i$ value, and preferably an $IC_{50}$ value and a $K_i$ value, of less than $1 \times 10^{-6}$, in particular less than $1 \times 10^{-7}$ and especially less than $1 \times 10^{-8}$ M.

Preferred compounds of formula 1 have a molecular weight of less than 2000 Da especially less than 1000 Da particularly less than 600 Da, e.g. less than 500 Da.

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

The invention embraces all combinations of preferred and more preferred groups and embodiments of groups recited above.

EXAMPLES

Biological Evaluation, Determination of $IC_{50}$- and $K_i$-Values of PEP-Inhibitors Recombinant human prolyl oligopeptidase was used for measurement. Recombinant expression was performed in *E. coli* under standard conditions as described elsewhere in the state of the art.

For activity measurements the chromogenic substrate Cbz-Gly-L-Pro-pNA was used in HEPES buffer pH 7.6 containing 50 mM HEPES, 200 mM NaCl, 1 mM EDTA, 1 mM DTT, 0.006% Brij35. Measurements were carried out at 30° C. Release of pNA were monitored continuously at 405 nm.

$IC_{50}$ values were determined using one substrate concentration (0.15 mM) and 11-15 serial dilutions of inhibitor starting with 0.1 mM. $IC_{50}$ values were calculated using non-linear regression to a 4-parameter equation (Prism 4.0, GraphPad).

For Ki determination 4 substrate (0.15 mM, 0.08 mM 0.04 mM, 0.02 mM) and 7 inhibitor concentrations in an appropriate range were used. Calculations were performed by multiple non-linear regression analysis to the equation for competitive inhibition using GraFit 5.0 Software (Erithacus Software).

IL-6 ELISA

To analyze basal secretion of IL-6, human glial U-343 cells were cultured in 6 well plates ($1.5 \times 10^6$ cells/well, Greiner) and treated with specific PEP inhibitors as indicated (20 μM each) for 24 hours in serum-free D-MEM medium (invitrogen). Aliquots of 40 μl conditioned medium were used to quantify the amount of secreted IL-6 by an human-specific IL-6 ELISA (Biosource) following the manufacturer's instructions. All data were obtained in quadruplicate. For the calculation of the IL-6 concentration in the cell culture medium after PEP-inhibitor treatment, the basal IL-6 concentration of the cell culture medium of untreated cell samples was set to 100%. The results of the measurement of the IL-6 concentration with PEP-inhibitor treated cells are presented as % of the untreated cell samples.

β-Amyloid ELISA

Cell Culture.

The human glioma cell line, U-343 and the human neuroblastoma cell line, SH-SY5Y were maintained in Dulbecco's modified Eagle's medium (DMEM) containing 10% fetal bovine serum (Gibco BRL, Karlsruhe, Germany) and incubated at 37° C. in a 5% $CO_2$ atmosphere. Culture media contained in general 60 μg/ml gentamycin (Gibco BRL, Karlsruhe, Germany).

Metabolic Labeling.

For the metabolic labeling approach, $5 \times 10^5$ cells were seeded in 35 mm culture dishes and then grown for 40 hours in the appropriate culture media. After washing, cells were incubated with [$^{35}$S]methionine (1 μCi/ml, ICN Biomedicals, Eschwege, Germany) in DMEM without L-methionine, L-cysteine and L-cystine (ICN Biochemicals) for 2 hours, followed by a 24-h chase with/without the PEP inhibitor Fmoc-Ala-Pyrr-CN (5 μM) at 37° C. in serum-free culture medium. The radiolabeled proteins in the chase medium were precipitated with 8% (w/v) TCA-solution and centrifuged at 15500×g for 10 min. After washing, the protein pellets were resuspended in 1 ml of distilled water and the radioactivity was measured in a Tri-carb2100TR-scintillation counter (Packard, Dreieich, Germany). All measurements were carried out at least in quadruplicate, and the experiment was repeated four times.

β-Amyloid ELISA.

To quantify intracellular and extracellular concentrations of β-amyloid peptides, 1-40 and 142, U-343 and SH-SY5Y cells were cultured in 6 well plates ($1.5 \times 10^6$ cells/well) and treated with specific PEP inhibitors (20 μM each) for 24 hours. For quantitation of secreted β-amyloid peptides the conditioned medium was collected and concentrated by lyophilisation. Likewise, after determination of the cell numbers/well (casy cell counter I, Schärfe System, Reutlingen, Germany), cells were lyzed with cell extraction buffer (Biosource, Solingen, Germany) according to the manufacturer's protocol. The protein concentration was determined by the method of Bradford (1976). Aliquots of 100 μl were used to quantify β-amyloid peptides 1-40 and 1-42 in quadruplicate by ELISA, (IBL, Hamburg, Germany) following the manufacturer's instructions. All obtained intracellular and extracellular concentrations were normalized to cell numbers and protein concentration, respectively.

For the calculation of the concentration of β-amyloid peptides 1-40 and 1-42 in the cell culture medium after PEP-inhibitor treatment, the basal concentration of β-amyloid peptides 1-40 and 1-42 in the cell culture medium of untreated cell samples was set to 100%. The results of the measurement of the concentration of β-amyloid peptides 1-40 and 1-42 with PEP-inhibitor treated cells are presented as % of the untreated cell samples.

The preferred PEP inhibitors of the present invention show a significant reduction of the IL-6 level and an increased β-amyloid secretion, especially of β-amyloid peptides 1-40 and 1-42. (see results shown in FIG. 1 and FIG. 2).

Inhibition of the Post-Cysteine Cleavage in the Peptide Humanin by Recombinant Human Prolyl Endopeptidase.

The degradation experiments are performed with recombinant human Prolyl Endopeptidase (rhPEP). The peptide humanin is used as substrate. The peptide humanin comprises 24 amino acids of the following sequence:

MAPRGFSCLLLLTSEIDLPVKRRA [SEQ ID NO: 1]

rhPEP is able to cleave humanin at two positions in the peptide sequence: after the proline residue in position 3 and after the cysteine residue at position 8.

The cleavage of humanin by PEP can be inhibited with specific PEP inhibitors of formula (I). The inhibitors of formula (I) prevent both the post proline and the subsequent post cysteine cleavage in the humanin sequence.

Experiment Description

All inhibitors are solved in 100% DMSO. The final concentration of the inhibitors in the stock solution is 2 mM. The DMSO stock solutions are stored at −20° C. The Humanin peptide is solved in 100% DMSO first and then is diluted with PEP buffer until a final concentration of 1 mg/ml, taking care that the final concentration of DMSO doesn't exceed 10% of this solution. The Humanin stock solution is stored at −20° C.

The enzymatic reaction is performed in PEP buffer, which consists of 270 mM HEPES (ROTH), 1080 mM NaCl (ROTH), 5,4 mM EDTA (MP Biomedicals), 0.03% 30-35 w/v BRIJ® Solution (Sigma Diagnostics), 7.96 mM DTT (Sigma).

The enzyme is stored at −20° C. in a 50% ethylene glycol stock solution.

Reaction Mixture

The rhPEP stock solution is diluted 1:20 in PEP buffer.

The inhibitor stock solutions are diluted 1:10 to 1:20 in water. Afterwards, the inhibitor solutions are mixed with an equal volume of 1 mg/ml Humanin stock solution in PEP buffer.

90 μl of the inhibitor/substrate solution is then mixed with 10 μl of enzyme solution. This mixture is incubated at 37° C. over the complete reaction time. The final inhibitor and substrate concentration is 80 μM (inhibitor) and 0.45 mg/ml (humanin) respectively.

The reaction is stopped at the following time points: 10, 30, 60, 120, 240, 480, 1440 minutes) by mixing 10 μl of the reaction mixture with 10 μl 0.1% TFA in water.

The identity and quantity of the different products resulting from the enzymatic hydrolysis were assessed by matrix-assisted laser desorption mass spectrometry. FIG. 3 shows the production of humanin cleavage product HN 9-24 in the presence of PEP. FIGS. 4 and 5 show that HN 9-24 is not produced in the presence of PEP when PEP inhibitors are present.

Example Compounds
| Example | Structure Mr (g/mol) | ESI-MS (M + H⁺) | IC$_{50}$ (M) | K$_i$ (M) | HPLC[a], Retention Time (min) | Extracellular IL-6 concentration[b], % of untreated cells | Extracellular Aβ-concentration, % of control |
|---|---|---|---|---|---|---|---|
| 1 | 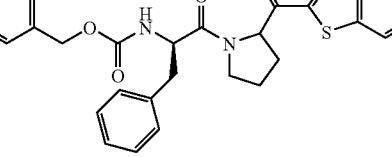 513.61 | 514.6 | $6.0 * 10^{-9}$ | $5.7 * 10^{-11}$ | 24.7 (A) | 14.3 | 447 |
| 2 | 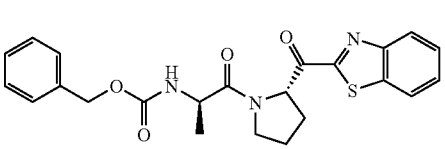 437.51 | 438.3 | $1.2 * 10^{-10}$ | $3.3 * 10^{-11}$ | 19.1 (A) | 20.1 | 123 |
| 3 | 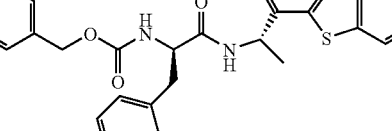 487.57 | 488.2 | $1.4 * 10^{-6}$ | n.d. | 23.5 (A) | 35.2 | 546 |
| 4 | 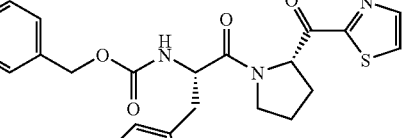 487.57 | 464.3 | $1.5 * 10^{-8}$ | $6.8 * 10^{-9}$ | 21.5 (A) | 14.6 | 519 |
| 5 | 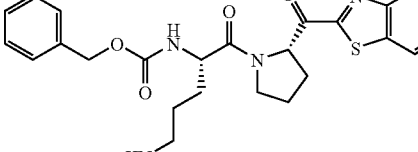 522.62 | 523.5 | $5.4 * 10^{-9}$ | $3.2 * 10^{-9}$ | 17.3 (A) | 109 | 94 |

-continued

| Example | Structure Mr (g/mol) | ESI-MS (M + H⁺) | $IC_{50}$ (M) | $K_i$ (M) | HPLC[a], Retention Time (min) | Extracellular IL-6 concentration[b], % of untreated cells | Extracellular Aβ-concentration, % of control |
|---|---|---|---|---|---|---|---|
| 6 | 463.55 | 482.2 | $1.7 \times 10^{-8}$ | $1.2 \times 10^{-8}$ | 18.8 (A) | 58 | 96.2 |
| 7 | 463.55 | 464.3 | $9.7 \times 10^{-9}$ | $8.2 \times 10^{-9}$ | 23.3 (A) | 17 | 528 |
| 8 | 494.61 | 495.4 | $2.0 \times 10^{-9}$ | $3.8 \times 10^{-11}$ | 16.5 (A) | 160 | 87.5 |
| 9 | 479.59 | 480.4 | $2.9 \times 10^{-8}$ | $6.0 \times 10^{-9}$ | 23.7' (A) | 33.1 | 368 |
| 10 | 387.45 | 388.4 | $4.3 \times 10^{-9}$ | $2.6 \times 10^{-9}$ | 13.7' (A) | 66 | 157 |

-continued

| Example | Structure Mr (g/mol) | ESI-MS (M + H⁺) | IC$_{50}$ (M) | K$_i$ (M) | HPLC[a], Retention Time (min) | Extracellular IL-6 concentration[b], % of untreated cells | Extracellular Aβ-concentration, % of control |
|---|---|---|---|---|---|---|---|
| 11 | 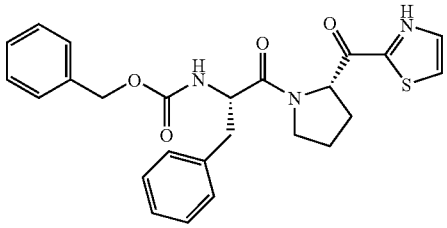 445.51 | 446.5 | 7.6 * 10⁻⁶ | 2.9 * 10⁻⁹ | 17.6' (B) | 52.1 | 340 |

[a]Gradient A or B, described in the experimental section, the corresponding gradient is mentioned in parenthesis.
[b]Calculated with the untreated control sample as basal level,n.d. means n.d. means "not determined".

General Synthetic Methods for the Preparation of the Starting Materials and the Examples The examples were prepared either via Route 1, Route 2 or via Route 3.

Starting materials for Route 1: Protected amino acid derivatives (W—KCONH—X—COOH, HN—Y—COR$^y$, R$^y$ typically represents OMe) were purchased from Bachem. Dipeptides (W—KCONH—X—CON—Y—COOH) were prepared via Method A and B (Intermediates E I, II, and C I, II) according to procedures of the literature (23). Starting material for Intermediate A IV was purchased from Bachem. The subsequent N-Methoxy-N-methyl derivatives (25) (Intermediate A III, IV and V) were prepared via 15 Method A.

Examples: The Intermediates A III, IV and V (Weinrebamides) were converted into the Examples 1, 2, 4, 9, 10 by the treatment with a solution of n-BuLi and the respective heteroaromatic compound via Method C (26). The heteroaromatic compounds were purchased from FLUKA or ALDRICH. A drawing is given in Scheme 2.

Starting materials for Route 2: Protected amino acid derivatives (Boc-NY—COOH) were purchased from Bachem and were reduced to obtain the Intermediates La I and II via Method D (24). Intermediates La I and II were oxidised to the corresponding Intermediates Lb I and II (aldehydes) with Swern Oxidation via Method E (24). Intermediates K I and II were prepared via Method F (U.S. Pat. No. 5,547,978). Intermediates K I and II were deprotected via Method G (23). Intermediates J I and II were coupled with W—KCO—NH—X—COOH via Method H.

Examples: The Intermediates H I-V were converted into the Examples 3, 5, 6, 7 by Swern Oxidation via Method E (Scheme 3). Example 8 was obtained by deprotection via Method G after oxidation.

Route 1:

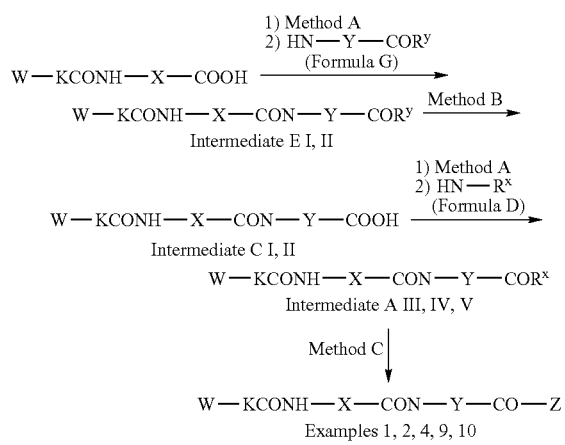

Scheme 2. Synthesis of Intermediates E, I, II (C-protected Dipeptides), Intermediates C I, II (Dipeptides), Intermediates A, III, IV and V (Weinrebamides), and Examples 1, 2, 4, 9, 10. Method A: mixed anhydride; Method B: saponification; Method C: n-BuLi, H-Z: heteroaryl compound.

Route 2:

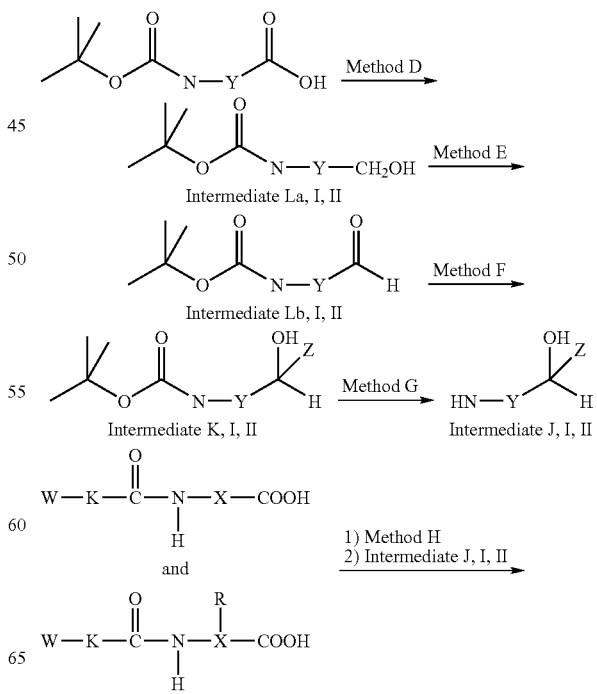

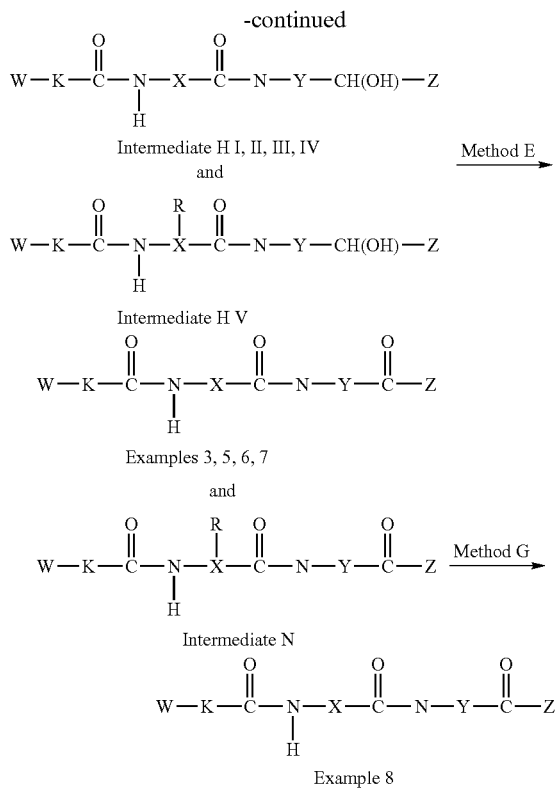

Scheme 3. Synthesis of the Intermediate La I, II (alcohols), Intermediates Lb I, II (aldehydes), Intermediates K I, II (protected heteroaryl compound components), Intermediates J I, II (deprotected heteroaryl compound components), Intermediates H I-V (heteroaryl-alcohols), and Examples 3, 5, 6, 7, and 8. Method D: 1.) mixed anhydride, 2.) LiAlH$_4$; Method E: Swern Oxidation; Method F: n-BuLi, H-Z: heteroaryl compound; Method G: TFA, TIPS; Method H: coupling reaction, R = Boc for the moiety of amino lysine.

Starting material for Route 3: Intermediate E I was prepared as described in Scheme 2.

Example: The Intermediate E I was converted into Example 11 by arylation with Grignard reagent (36) via Method J (Scheme 4).

Route 3:

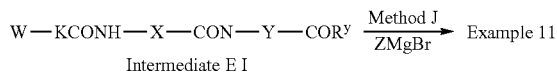

Intermediate E I

Scheme 4. Synthesis of Example 11. Method J: MeMgBr in Et$_2$O, pyrrole; ZMgBr was formed in situ.

| Abbrevations | |
|---|---|
| Aloc | Allyloxycarbonyl |
| Boc | tert.-Butyloxycarbonyl |
| n-BuLi | n-Butyllithium |
| Cbz | Benzyloxycarbonyl |
| EE | Ethyl acetate |
| EtOH | Ethanol |
| Et$_2$O | Diethyl ether |
| LiAlH$_4$ | Lithium aluminium hydride |
| NEt$_3$ | Triethylamine |
| NMM | 4-Methylmorpholine |
| pNA | 4-Nitroanilide |
| TFA | Trifluoroacetic acid |
| TIPS | Triisopropylsilane |
| TLC | Thin Layer Chromatography |

Analytical Methods

NMR spectra were performed on Bruker AM 400 and Varian Unity 500 spectrometers. The following abbreviations are used: s (singlet), d (doublet), dd (doublet of doublets), t (triplet), and m (multiplet). ESI-MS: Mass spectra were taken with an MDS Sciex API 365 mass spectrometer equipped with an Ionspray™ interface (MDS Sciex; Thorn Hill, ON, Canada). The instrument settings, data acquisition and processing were controlled by the Applied Biosystems (Foster Clty, Calif., USA) Analyst™ software for Windows NT™. 50-100 scans were performed by the positive ionization Q1 scan mode to accumulate the peaks. Sample solutions were diluted with 50% methanol in 0.5% formic acid to reach concentrations about 10 μg/ml. Each sample solution was introduced directly by a microsyringe (1 ml) through an infusion pump (Havard Apparatus 22; Havard Instruments; Holliston, Mass., USA) and fused silica capillary tubing at a rate of 20 ul/min. Thin layer chromatography (TLC) was done using Macherey Nagel Polygram® SIL G/UV$_{245}$. Visualisation was accomplished by means of UV light at 254 nm, followed by dyeing with potassium permanganate or Cer-Molybdate-solution. Solvents were distilled prior to use. All commercially available reagents were used without further purification. Aloc-L-Phe-OMe and the other amino acid derivates were purchased from Bachem. The pH-7 buffer solution used in the workup procedures was prepared by dissolving potassium dihydrogen phosphate (85.0 g) and sodium hydroxide (14.5 g) in water (1 l). Analytical HPLC was performed using a Merck-Hitachi device: acetonitrile-water (flow rate: 1 ml min$^{-1}$), column: LiChrosphere 5 um RP18e, 125×4.0 mm (Merck), pump: L-7100 Merck-Hitachi was used. Gradient A was used for the detection of the purified compounds in the examples. Characterisation of gradient A: starting from acetonitrile-water (5/95) at t=0 min to acetonitrile-water (60/40) within 20 min, to acetonitrile-water (95/5) after additional 10 min. Characterisation of gradient B: starting from acetonitrile-water (20/80) at t=0 min to acetonitrile-water (95/5) within 30 min.

Specific Synthesis and Analytical Information for Starting Materials and Certain Compounds General Methods Method A (Conversion of carboxylic acid to mixed anhydride): The N-protected amino acid derivative (W—KCONH—X—COOH or W—KCONH—X—CON—Y—COOH, 1.0 equiv.) was dissolved in dry THF and cooled to −15° C. NMM (1.0 equiv.) was added. Isobutyl chloroformate (1.0 equiv.) was added dropwise. Method generates Intermediates E I, II and A III, IV, V.

Method B (Ester hydrolysis): The ester (Intermediate E I, II; 1.0 equiv.) was dissolved in EtOH and 1 M NaOH was added (2.3 equiv.). The reaction mixture was stirred at room temperature and the conversion was checked by TLC. At the final end of conversion the pH of the mixture was adjusted to 2-3 with 1 N HCl. The organic material was extracted five times with EE. The combined organic layers were dried over Na$_2$SO$_4$ and concentrated under reduced pressure. The crude compound was purified by flash chromatography generating Intermediate C I, II.

Method C (Metallation and Alkylation): A stirred solution of the heteroaryl compound (H—Z, 3.0 equiv.) in dry THF was cooled to −50° C. n-BuLi (3.0 equiv.) was added dropwise. After 10 minutes, a solution of (Intermediate A III, IV; 1.0 equiv.) in dry THF was added dropwise. The mixture was stirred for 30 minutes before the mixture was diluted with pH-7 buffer solution. The product was extracted with EE. The solvent was dried over $Na_2SO_4$, filtered and evaporated under reduced pressure. The crude compound was purified by flash chromatography generating Examples 1, 2, 4, 9, and 10.

Method D (Reduction of carboxylic acid to alcohol): A mixed anhydride of a protected amino acid derivate (1.0 equiv.) was prepared according to Method A, filtered under an atmosphere of argon and cooled to −20° C. $LiAlH_4$ (1.5 equiv.) was added in portions in order to control the progress of the reaction. The mixture was stirred at −20° C. for 1 h and at room temperature for 2 h. The reaction mixture was hydrolysed with a 1 M $KHSO_4$ solution at 0° C. After warming to room temperature the crude product was extracted with EE, dried over $Na_2SO_4$, filtered and evaporated under reduced pressure. Intermediate La I, II were used without further purification. Method generates Intermediates La I, II.

Method E (Swern oxidation of alcohol to aldehyde): A stirred solution of oxalyl chloride (1.2 equiv.) in dry $CH_2Cl_2$ was cooled to −70° C. DMSO (2.6 equiv.) was added dropwise and the mixture was stirred for 30 minutes. A solution of the alcohol (Intermediate La I, II) in dry $CH_2Cl_2$ was added dropwise and the mixture was stirred for 2 h. $NEt_3$ (5.0 equiv.) was added and the mixture was allowed to warm to room temperature. The reaction mixture was diluted with water. After separation of the layers the organic phase was washed with water and brine and dried over $Na_2SO_4$. After filtration the solvent was evaporated under reduced pressure. The crude compound was purified by flash chromatography generating the Intermediate Lb I, II, N and Examples 3, 5, 6, 7.

Method F (Metallation and Arylation): A stirred solution of the heteroaryl compound (H—Z) (1.1 equiv.) in dry THF was cooled to −78° C. n-BuLi (1.15 equiv.) was added dropwise. After 10 minutes, a solution of Intermediate Lb I, II (1.0 equiv.) in dry THF was added dropwise. The mixture was stirred for 30 minutes before the mixture was diluted with pH-7 buffer solution. The product was extracted with EE. The solvent was dried over $Na_2SO_4$, filtered and evaporated under reduced pressure. The crude compound was purified by flash chromatography generating the Intermediate K I, II.

Method G (Deprotecting a protecting group): TFA (7.5 ml) was added to a mixture of the protected compound (Intermediate K I, II; 1.0 equiv.) and TIPS (2.5 equiv.) in dry $CH_2Cl_2$ (10 ml). This solution was stirred for 2 h at room temperature before it was diluted with toluol. The solvents were removed under reduced pressure and the obtained residue was used due to instability without further purification generating the Intermediate J I, II. This method was used to generate Example 8.

Method H (Coupling reaction): The protected amino acid derivate (W—KCONH—X—COOH), 1.0 equiv.) was dissolved in dry DMF. To this mixture, HATU (1.0 equiv.), HOAt (1.0 equiv.), Intermediate J I, II (1.0 equiv.) and N-ethyldiisopropylamine (2.0 equiv.) were added and the whole mixture was stirred overnight. The solvent was evaporated in vacuo by using an oil pump. The obtained crude compound was dissolved in EE, washed with 1 N HCl, water, aqueous $NaHCO_3$, water and brine and dried over $Na_2SO_4$. After filtration the solvent was evaporated under reduced pressure. The crude compound was purified by flash chromatography generating Intermediate H I, II, III, IV and V.

Method J (Arylation with Grignard reagent): A solution of methylmagnesium bromide (3.0 M in $Et_2O$, 8.0 equiv.) in toluene (15 ml) was cooled to −30° C. and treated with Z—H (pyrrole) (12 equiv.). After stirring for 10 minutes at −30° C., the solution was warmed up to 0° C. and stirred for 30 minutes and was then cooled to −60° C. This prepared Grignard-solution was added to a solution of Intermediate E I in toluene (3 ml), which was cooled to −60° C. The mixture was stirred overnight and was allowed to warm to room temperature. The mixture was diluted with pH-7 buffer solution, diluted with EE and filtered. After separation of the layers, the water phase was extracted with EE (2×), dried over $Na_2SO_4$, filtered and evaporated under reduced pressure. The crude product was purified by flash chromatography generating Example 11.

Intermediates

Intermediate E I: Cbz-L-Phe-L-Pro-OMe

A mixed anhydride was prepared according to Method A (W—KCONH—X—COOH: Cbz-L-Phe-OH). After stirring for 15 minutes, 1.0 equiv. of HCl.H-L-Pro-OMe in dry THF and NMM (1.0 equiv.) were added. The mixture was stirred overnight, during which time it was allowed to warm to room temperature. The solvent was evaporated in vacuo and the obtained residue was dissolved in EE, washed with 1 N HCl, water, aqueous $NaHCO_3$, water and brine and dried over $Na_2SO_4$. After filtration the solvent was evaporated under reduced pressure. The crude compound was purified by flash chromatography generating Intermediate E I, yield of the purified compound: 72%.

Intermediate E II: Cbz-L-Ala-L-Pro-OMe

Intermediate E II was prepared as described for Intermediate E I above (W—KCONH—X—COOH: Cbz-L-Ala-OH; HN—Y—COR$^y$: HCl.H-L-Pro-OMe), yield of the purified compound: 92%.

Intermediate C I: Cbz-L-Phe-L-Pro-OH

Intermediate C I was prepared according to Method B, yield of the purified compound: 94%.

Intermediate C II: Cbz-L-Ala-L-Pro-OH

Intermediate C II was prepared according to Method B, yield of the purified compound: 91%.

Intermediate A III: Cbz-L-Phe-L-Pro-N($CH_3$)$OCH_3$

A mixed anhydride was prepared according to Method A (W—KCONH—X—CON—Y—COOH: Cbz-L-Phe-L-Pro-OH). After stirring for 15 minutes, 1.0 equiv. of HCl.HN($CH_3$)$OCH_3$ in dry THF and NMM (1.0 equiv.) were added. The mixture was stirred overnight, during which time it was allowed to warm to room temperature. The solvent was evaporated in vacuo and the obtained residue was dissolved in EE, washed with 1 N HCl, water, aqueous $NaHCO_3$, water and brine and dried over $Na_2SO_4$. After filtration the solvent was evaporated under reduced pressure. The crude compound was purified by flash chromatography generating Intermediate A Ill, yield of the purified compound: 81%.

Intermediate A IV: Cbz-L-Ala-L-Pro-N($CH_3$)$OCH_3$

Intermediate A IV was prepared as described for Intermediate A III above (W—KCONH—X—CON—Y—COOH: Cbz-L-Ala-L-Pro-OH; H—R$^x$: HCl.HN($CH_3$)$OCH_3$), yield of the purified compound: 98%.

Intermediate A V: Boc-L-Phe-L-Pro-N($CH_3$)$OCH_3$

Intermediate A V was prepared as described for Intermediate A III above (W—KCONH—X—CON—Y—COOH: Boc-L-Phe-L-Pro-OH (purchased from Bachem); H—R$^x$: HCl.HN($CH_3$)$OCH_3$), yield of the purified compound: 59%.

Intermediate La I: Boc-L-Alaninol

Intermediate La I was prepared according to Method D, the generated alcohol was used without further purification, yield of the crude compound: 48%.

Intermediate La II: Boc-L-Prolinol

Intermediate La II was prepared according to Method D, the generated alcohol was used without further purification, yield of the crude compound: 79%.

Intermediate Lb I: Boc-L-Ala-Aldehyde

Intermediate Lb I was prepared according to Method E and purified by flash chromatography, yield of the purified compound: 60%.

Intermediate Lb II: Boc-L-Pro-Aldehyde

Intermediate Lb II was prepared according to Method E and purified by flash chromatography, yield of the purified compound: 58%.

Intermediate K I: tert.-Butyl (2S)-1-(benzo[d]thiazol-2-yl)-1-hydroxypropan-2-ylcarbamate Intermediate K I was prepared according to Method F, yield of the purified compound: 30%.

Intermediate K II: (S)-tert.-Butyl 2-((R)-(benzo[d]thiazol-2-yl)(hydroxy)methyl)-pyrrolidine-1-carboxylate Intermediate K II was prepared according to Method F, yield of the purified compound: 49%.

Intermediate J I: (2S)-2-Amino-1-(benzo[d]thiazol-2-yl)propan-1-ol

Intermediate J I was prepared according to Method G. The compound was used without further purification due to instability.

Intermediate J II: (R)-(Benzo[d]thiazol-2-yl)((S)-pyrrolidin-2-yl)methanol

Intermediate J II was prepared according to Method G. The compound was used without further purification due to instability.

Intermediate H I: Benzyl (1S)-1-((2R)-1-(benzo[d]thiazol-2-yl)-1-hydroxypropan-2-ylcarbamoyl)-2-phenylethylcarbamate Intermediate H I was prepared according to Method H coupling Cbz-L-Phe-OH (W—KCONH—X—COOH) and Intermediate J I, yield of the purified compound: 29%.

Intermediate H II: Benzyl (1S)-1-((S)-2-((R)-(benzo[d]thiazol-2-yl)(hydroxy)-methyl)pyrrolidin-1-yl)-1-oxohexylguanyl-2-ylcarbamate Intermediate H II was prepared according to Method H coupling Cbz-L-Arg-OH (W—KCONH—X—COOH) and Intermediate J II, yield of the purified compound: 50%.

Intermediate H III: Benzyl (1S)-1-(((2R)-1-(benzo[d]thiazol-2-yl)(hydroxy)methyl)-pyrrolidin-1-yl)-2-carboxyethylcarbamate Intermediate H III was prepared according to Method H coupling Cbz-L-Asp(OtBu)-OH (W—KCONH—X—COOH) and Intermediate J II (yield of the purified compound: 46%), followed by Method G generating Intermediate H III (yield of the purified compound: 35%).

Intermediate H IV: Allyl (1S)-1-(((2R)-1-(benzo[d]thiazol-2-yl)(hydroxy)methyl)-pyrrolidin-1-yl)-2-phenylethylcarbamate Intermediate H IV was prepared according to Method H coupling Aloc-L-Phe-OH (W—KCONH—X—COOH) and Intermediate J I. Yield of the purified Intermediate H IV: 71%.

Intermediate H V: Benzyl (1S)-1-(((2R)-1-(benzo[d]thiazol-2-yl)(hydroxy)methyl)-pyrrolidin-1-yl)-2-(4-tert.butyloxycarbonylaminobutyl)-carbamate Intermediate H V was prepared according to Method H coupling Z-L-Lys(Boc)-OH (W—KCONH—X—COOH) and Intermediate J II. Yield of the purified Intermediate H V: 33%.

Intermediate N: Benzyl (1S)-1-(((2R)-1-(benzo[d]thiazol-2-yl)(oxymethyl)-pyrrolidin-1-yl)-2-(4-tert.butyloxycarbonylaminobutyl)-carbamate Intermediate N was prepared according to Method E, yield of the purified Intermediate N: 24%.

EXAMPLES

Example 1

2-[Cbz-L-Phe-L-Pro]Benzothiazole

Example 1 was prepared according to Route 1 via Intermediate E I, Intermediate C I, Intermediate A III and Method C (H—Z: Benzothiazole, yield of the purified compound: 82%).

Example 2

2-[Cbz-L-Ala-L-Pro]Benzothiazole

Example 2 was prepared according Route 1 via Intermediate E II, Intermediate C II, Intermediate A IV and Method C (H—Z: Benzothiazole, yield of the purified compound: 17%).

Example 3

2-[Cbz-L-Phe-L-Ala]Benzothiazole

Example 3 was prepared according to Route 2 via Intermediate La I, Intermediate Lb I, Intermediate K I, Intermediate J I, Intermediate H I, Method E (yield of the purified compound: 28%).

Example 4

2-[Cbz-L-Phe-L-Pro]Thiazole

Example 4 was prepared according to Route 1 via Intermediate E I, Intermediate C I, Intermediate A III and Method C (H—Z: Thiazole, yield of the purified compound: 19%).

Example 5

2-[Cbz-L-Arg-L-Pro]Benzothiazole

Example 5 was prepared according to Route 2 via Intermediate La II, Intermediate Lb II, Intermediate K II, Intermediate J II, Intermediate H II, Method E (yield of the purified compound: 38%).

Example 6

2-[Cbz-L-Asp-L-Pro]Benzothiazole

Example 6 was prepared according to Route 2 via Intermediate La II, Intermediate Lb II, Intermediate K II, Intermediate J II, Intermediate H III, Method E (yield of the purified compound: 24%).

Example 7

2-[Aloc-L-Phe-L-Pro]Benzothiazole

Example 7 was prepared according to Route 2 via Intermediate La II, Intermediate Lb II, Intermediate K II, Intermediate J II, Intermediate H IV and Method E (yield of the purified compound: 20%).

Example 8

2-[Cbz-L-Lys-L-Pro]Benzothiazole

Example 8 was prepared according to Route 2 via Intermediate La II, Intermediate Lb II, Intermediate K II, Intermediate J II, Intermediate H V, Intermediate N and Method G (yield of the purified compound for synthesis step of Method G: 100%).

Example 9

2-[Boc-L-Phe-L-Pro]Benzothiazole

Example 9 was prepared according to Route 1 via the Dipeptide Intermediate A V and Method C (H—Z: Benzothiazole, yield of the purified compound: 24%).

Example 10

2-[Cbz-L-Ala-L-Pro]Thiazole

Example 10 was prepared according to Route 1 via Intermediate E II, Intermediate C II, Intermediate A IV and Method C (H—Z: Thiazole, yield of the purified compound: 7%).

Example 11

2-[Cbz-L-Ala-L-Pro]Pyrrole

Example 11 was prepared according to Route 3 via Intermediate E I and Method J (yield of the purified compound: 35%).

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned above are herein incorporated in their entirety by reference.

---

The invention claimed is:

1. A compound of the general formula 1, or a pharmaceutically acceptable salt thereof, including all or stereoisomers:

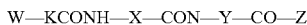  formula 1 wherein

W represents alkyl, alkenyl, alkynyl, cycloalkyl, -heterocyclyl, carbocyclyl, aryl, -alkylaryl or -alkylheteroaryl;

K represents O, NH or $CH_2$;

or K is absent and W—CO represents the moiety of an amino acid or aza-amino acid;

NH—X—CO represents the moiety of non-cyclic amino acid or non-cyclic aza-amino acid, wherein when NH—X—CO represents the moiety of Asp or Glu the acid side chain of said Asp or Glu may optionally be joined via a peptide bond to another amino acid or aza-amino acid;

N—Y—CO— is selected from a moiety of formula 2a, 2b, 2c, 2d, 2e, 2f, or 2g:

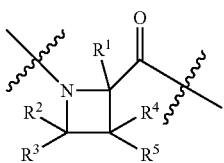

2a

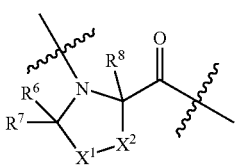

2b

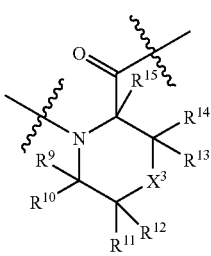

2c

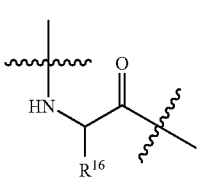

2d

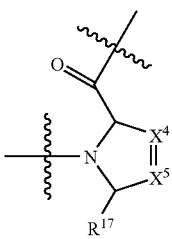

2e

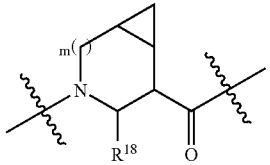

2f

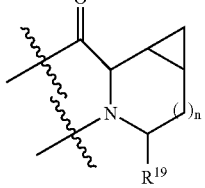

2g wherein $R^1$-$R^{15}$ and $R^{17}$-$R^{19}$ are independently H or an alkyl chain, alkenyl chain, alkynyl chain, cycloalkyl, a carbocycle, aryl, heteroaryl, heterocycle, or a group selected from halogen, amino, —$CONH_2$, CONH(alkyl), —CON(alkyl)$_2$, nitro, hydroxyl, —CN and —SCN;

or else $R^2/R^3$, $R^4/R^5$, $R^6/R^7$, $R^9/R^{10}$, $R^{11}/R^{12}$ together with the carbon atom to which they are attached independently represent oxo;

or else $R^3$ and $R^5$ are connected to form a benzene ring fused to the azetidine ring (in which case $R^2$ and $R^4$ are absent) or $R^{10}$ and $R^{11}$ are connected to form a benzene ring fused to the piperidine ring (in which case $R^9$ and $R^{12}$ are absent);

$R^{16}$ is the side chain of an amino acid moiety;

$X^1$ is $CR^{20}R^{21}$, O, S, SO, $SO_2$ or $NR^{22}$;

$X^2$ is $CR^{23}R^{24}$, O, S, SO, $SO_2$ or $NR^{25}$;

$X^3$ is $CR^{26}R^{27}$, O, S, SO, $SO_2$ or $NR^{28}$;

$R^{22}$, $R^{25}$ and $R^{28}$, independently of each other, are H, alkyl, alkenyl, alkynyl, cycloalkyl, carbocycle heterocycle, aryl, heteroaryl, aryl-alkyl or a heteroaryl-alkyl group;

$R^{20}$, $R^{21}$, $R^{23}$, $R^{24}$, $R^{27}$ and $R^{28}$, independently of each other, are H, alkyl, alkenyl, alkynyl, cycloalkyl, carbocycle heterocycle, aryl, heteroaryl, aryl-alkyl, heteroaryl-alkyl group or, a carbaldehyde (—CHO), a ketone group (—CO—$R^{29}$), a boronic acid group (—B(OH)$_2$), a cyano group (—C≡N), a carboxylic acid group (—COOH), a carboxylic acid ester group (—COOR$^{30}$), a carboxylic acid anhydride group (—CO—O—CO—$R^{31}$), a hydroxamic acid group (—CO—NH(OH)), a N-substituted hydroxamic acid group (—CO—NR$^{32}$(OH)), a O-substituted hydroxamic acid group (—CO—NH(OR$^{33}$)), a carboxamide group (—CO—$NH_2$), a N-substituted or N,N-disubstituted carboxylic acid amide group, (—CO—NHR$^{34}$; —CO—NR$^{35}$R$^{36}$), an amido group (—HN—CO—R$^{37}$), a sulfonic acid group (—$SO_3H$), a sulfonamide group (—$SO_2$—$NH_2$), a N-substituted or N,N-disubstituted sulfonamide group (—$SO_2$—NHR$^{38}$; —$SO_2$—NR$^{39}$R$^{40}$), an amidosulfone group (—NH—$SO_2$—R$^{41}$), a sulfone group (—$SO_2$—R$^{42}$), a phosphoric acid group (—OP(=O)(OH)$_2$), a phosphoric acid ester group (—OP(=O)(OR$^{43}$)(OR$^{44}$)), a phosphonic acid group (—P(=O)(OH)$_2$), an phosphonic acid ester group (—P(=O)(OR$^{45}$)(OR$^{46}$)), a halogeno group, a trifluormethyl group (—$CF_3$), a thiol group (—SH); a thioether group (—S—R$^{47}$), a hydroxy group (—OH); an alkoxy group (—O—R$^{48}$), a tetrazole group, an amino group (—NH₂), or a N-substituted or N,N-disubstituted amino group (—NHR⁴⁹; —NR⁵⁰R⁵¹); or when X¹ is CR²⁰R²¹, R⁶ and R²⁰ may be connected to form a benzene ring fused to the pyrrolidine ring (in which case R⁷ and R²¹ are absent), or when X² is CR²²R²³, R²⁰ and R²² may be connected to form a benzene ring fused to the pyrrolidine ring (in which case R²¹ and R²³ are absent); or when X³ is CR²⁶R²⁷, R¹¹ and R²⁶ may be connected to form a benzene ring fused to the piperidine ring (in which case R¹² and R²⁷ are absent), or R²⁷ and R¹³ may be connected to form a benzene ring fused to the piperidine ring (in which case R²⁶ and R¹⁴ are absent);

the substituents R²⁹, R³⁰, R³¹, R³², R³³, R³⁴, R³⁵, R³⁶, R³⁷, R³⁸, R³⁹, R⁴⁰, R⁴¹, R⁴², R⁴³, R⁴⁴, R⁴⁵, R⁴⁶, R⁴⁷, R⁴⁸, R⁴⁹, R⁵⁰, and R⁵¹, independently of each other are H or an alkyl, alkenyl, alkynyl, cycloalkyl, carbocycle, heterocycle, aryl, heteroaryl, aryl-alkyl- or heteroaryl-alkyl-, group; and alternatively, the pairs R³⁵R³⁶, R³⁹R⁴⁰ and R⁵⁰R⁵¹, independently of each other, may, together with the nitrogen to which they are attached, form a part of a heterocycle ring (eg pyrrolidine, piperidine or morpholine); or the pairs R⁴³/R⁴⁴, R⁴⁵/R⁴⁶ may be linked to form a $C_{1-4}$ alkylene chain;

X⁴ is CR⁵² or N;

X⁵ is CR⁵³ or N;

R⁵² and R⁵³, independently of each other, are H, alkyl, alkenyl, alkynyl, cycloalkyl, carbocycle, heterocycle, aryl, heteroaryl, aryl-alkyl, heteroaryl-alkyl, aryl-heteroalkyl, heteroaryl-heteroalkyl group or, a carbaldehyde (—CHO), a ketone group (—CO—R⁵⁴), a boronic acid group (—B(OH)₂), a cyano group (—C≡N), a carboxylic acid group (—COOH), a carboxylic acid ester group (—COOR⁵⁵), a carboxylic acid anhydride group (—CO—O—CO—R⁵⁶), a hydroxamic acid group (—CO—NH(OH)), a N-substituted hydroxamic acid group (—CO—NR⁵⁷(OH)), a O-substituted hydroxamic acid group (—CO—NH(OR⁵⁸)), a carboxamide group (—CO—NH₂), a N-substituted or N,N-disubstituted carboxylic acid amide group, (—CO—NHR⁵⁹; —CO—NR⁶⁰R⁶¹), an amido group (—HN—CO—R⁶²), a sulfonic acid group (—SO₃H), a sulfonamide group (—SO₂—NH₂), a N-substituted or N,N-disubstituted sulfonamide group (—SO₂—NHR⁶³; —SO₂—NR⁶⁴R⁶⁵), an amidosulfone group (—NH—SO₂—R⁶⁶), a sulfone group (—SO₂—R⁶⁷), a phosphoric acid group (—OP(=O)(OH)₂), a phosphoric acid ester group (—OP(=O)(OR⁶⁸)(OR⁶⁹)), a phosphonic acid group (—P(=O)(OH)₂), an phosphonic acid ester group (—P(=O)(OR⁷⁰)(OR⁷¹)), a halogeno group, a trifluormethyl group (—CF₃), a thiol group (—SH); a thioether group (—S—R⁷²), a hydroxy group (—OH); an alkoxy group (—O—R⁷³), a tetrazole group, an amino group (—NH₂), or a N-substituted or N,N-disubstituted amino group (—NHR⁷⁴; —NR⁷⁵R⁷⁶);

the substituents R⁵⁴, R⁵⁵, R⁵⁶, R⁵⁷, R⁵⁸, R⁵⁹, R⁶⁰, R⁶¹, R⁶², R⁶³, R⁶⁴, R⁶⁵, R⁶⁶, R⁶⁷, R⁶⁸, R⁶⁹, R⁷⁰, R⁷¹, R⁷², R⁷³, R⁷⁴, R⁷⁵, and R⁷⁶, independently of each other are H or an alkyl, alkenyl, alkynyl, cycloalkyl, carbocycle, heterocycle, aryl, heteroaryl, aryl-alkyl, heteroaryl-alkyl group; and alternatively, the pair R⁵²/R⁵³ if present, together with the carbon atoms to which they are attached may form part of a heterocycle or carbocycle ring; or the pairs R⁶⁰R⁶¹, R⁶⁴R⁶⁵, and R⁷⁵R⁷⁶, independently of each other, may, together with the nitrogen to which they are attached, form a part of a heterocycle ring (eg pyrrolidine, piperidine or morpholine); or the pairs R⁶⁸/R⁶⁹ and R⁷⁰/R⁷¹ may be linked to form a $C_{1-4}$ alkylene chain;

m represents an integer 0 to 2;

n represents an integer 0 to 2;

Z is heteroaryl, and with the proviso that the following compound:

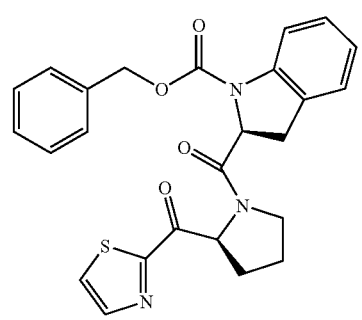

(a)

is excluded from formula 1.

2. A compound according to claim 1, wherein R¹-R¹⁵ and R¹⁷-R¹⁹ independently represent H, halogen, CN or alkyl.

3. A compound according to claim 1, wherein R¹-R¹⁵ and R¹⁷-R¹⁹ are H.

4. A compound according to claim 1, wherein X¹, X² and X³ independently represent CH₂ or CHMe.

5. A compound according to claim 1, wherein X⁴ and X⁵ independently represent CH or CMe.

6. A compound according to claim 1, wherein R²⁰, R²¹, R²³, R²⁴, R²⁶, R²⁷, R²⁸, R⁵² and R⁵³ are H.

7. A compound according to claim 1, wherein m and n independently represent 0 or 1.

8. A compound according to claim 7, wherein m and n are 0.

9. A compound according to claim 1, wherein W represents -alkylaryl, -alkylheteroaryl, alkyl, alkenyl, alkynyl or cycloalkyl.

10. A compound according to claim 9, wherein W represents alkenyl-, alkyl- or arylalkyl-.

11. A compound according to claim 10, wherein W is arylalkyl-.

12. A compound according to claim 9, wherein W is selected from the group consisting of -methylaryl, methylheteroaryl, $C_{2-6}$ alkenyl and $C_{2-6}$ alkyl.

13. A compound according to claim 9, wherein aryl represents phenyl optionally substituted by alkyl and/or halo.

14. A compound according to claim 9, wherein heteroaryl represents pyridyl optionally substituted by alkyl and/or halo.

15. A compound according to claim 1, wherein W—K—CO represents allyloxycarbonyl (Aloc), t-butyloxycarbonyl (Boc) or benzyloxycarbonyl (Cbz).

16. A compound according to claim 15, wherein W—K—CO is benzyloxycarbonyl.

17. A compound according to claim 1, wherein K represents O or CH₂, especially O.

18. A compound according to claim 1 wherein NH—X—CO represents the moiety of a non-cyclic amino acid.

19. A compound according to claim 1, wherein NH—X—CO represents a proteinogenic amino acid.

20. A compound according to claim 19, wherein NH—X—CO is selected from the group consisting of L-Ala, L-Arg, L-Asp and L-Phe.

21. A compound according to claim 1, wherein N—Y—CO represents a moiety of formula 2d.

22. A compound according to claim 1, wherein $R^{16}$ represents the sidechain of a proteinogenic amino acid.

23. A compound according to claim 22, wherein $R^{16}$ represents H, methyl, —CH$_2$OH, —CH(Me)OH, CHMe$_2$, CH$_2$CHMe$_2$, CH(Me)CH$_2$Me, CH$_2$CH$_2$CONH$_2$, —CH$_2$COOH, —CH$_2$CONH$_2$ or CH$_2$CH$_2$COOH.

24. A compound according to claim 23, wherein $R^{16}$ represents alkyl.

25. A compound according to claim 24, wherein $R^{16}$ is methyl.

26. A compound according to claim 1, wherein N—Y—CO represents a moiety of formula 2a, 2e, 2f or 2g.

27. A compound according to claim 1, wherein N—Y—CO represents a moiety of formula 2b or 2c.

28. A compound according to claim 1, wherein N—Y—CO represents a moiety of formula of 2h or 2i:

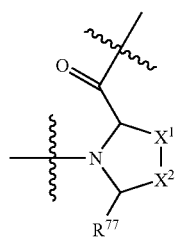

2h

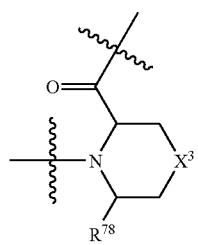

2i wherein $R^{77}$ and $R^{78}$ independently represent H, halogen, CN or alkyl.

29. A compound according to claim 1, wherein N—Y—CO represents a moiety of formula 2j or 2k:

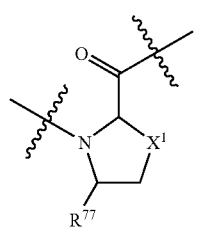

2j

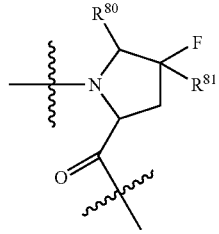

2k wherein $R^{77}$ is H, halogen, CN or alkyl, and
$R^{80}$ and $R^{81}$ are independently H or fluoro.

30. A compound according to claim 28, wherein $R^{77}$ and $R^{78}$ independently are methyl.

31. A compound according to claim 28, wherein $R^{77}$ and $R^{78}$ independently are CN.

32. A compound according to claim 28, wherein $R^{77}$ and $R^{78}$ independently are H.

33. A compound according to claim 1 wherein $X^1$ represents CH$_2$.

34. A compound according to claim 1, wherein Z represents a 5-membered heteroaryl ring optionally fused to a benzene ring.

35. A compound according to claim 34, wherein Z is selected from the group consisting of 2-furan, 2-imidazole, 2-thiazole, 4-thiazole, 5-thiazole, 2-thiophene, 3-thiophene, 2-oxazole, 4-oxazole, 5-oxazole, 2-pyrrole, 3-pyrrole, 2-benzo[d]imidazole, 2-benzo[d]thiazole, 2-benzo[b]thiophene, 3-benzo[b]thiophene, 2-benzo[d]oxazole, 2-indole, 3-indole, or from a moiety of formula 3a, 3b, 3c, 3d or 3e:

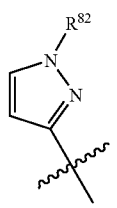

3a

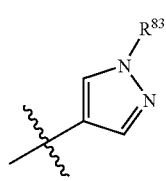

3b

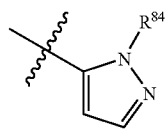

3c

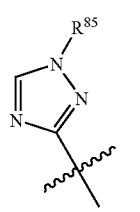

3d

-continued

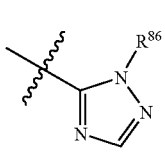
3e wherein $R^{82}$, $R^{83}$, $R^{84}$, $R^{85}$ and $R^{86}$ are independently H or an alkyl chain, alkenyl chain, alkynyl chain, cycloalkyl, a carbocycle, aryl, heteroaryl, heterocycle, or a group selected from halogen, amino, —CONH$_2$, CONH(alkyl), —CON(alkyl)$_2$, nitro, hydroxyl, oxo, —CN and —SCN.

36. A compound according to claim 35, wherein $R^{82}$, $R^{83}$, $R^{84}$, $R^{85}$ and $R^{86}$ are H or alkyl.

37. A compound according to claim 36, wherein $R^{82}$, $R^{83}$, $R^{84}$, $R^{85}$ and $R^{86}$ are H.

38. A compound according to claim 1 corresponding to Example 1:

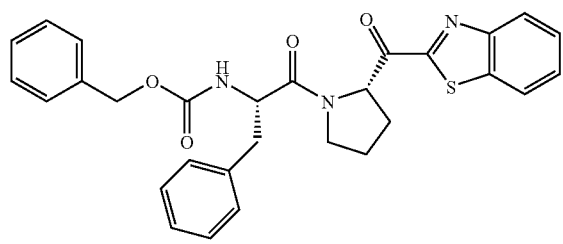

or a pharmaceutical salt, or stereoisomer.

39. A compound according to claim 1 corresponding to any one of the Examples 2-7 or a pharmaceutical salt, or stereoisomer:

2

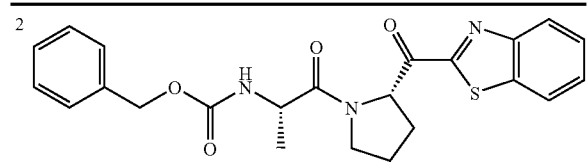

3

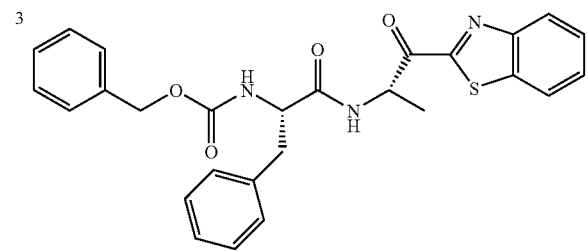

-continued

4

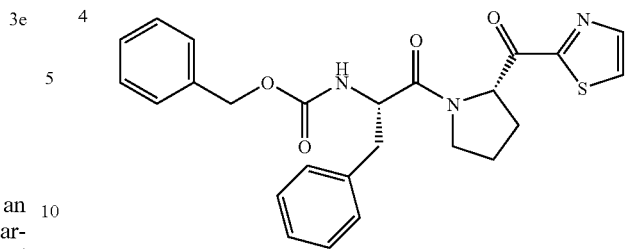

5

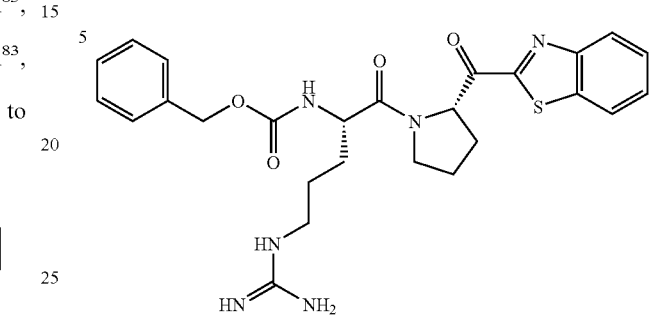

6

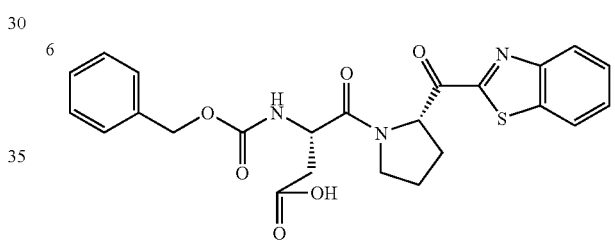

7

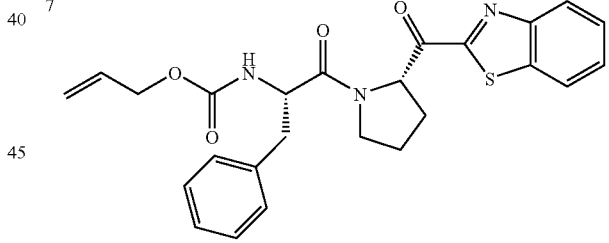

40. A compound according to claim 1 corresponding to any one of the Examples 8-11 or a pharmaceutical salt, or stereoisomer:

8

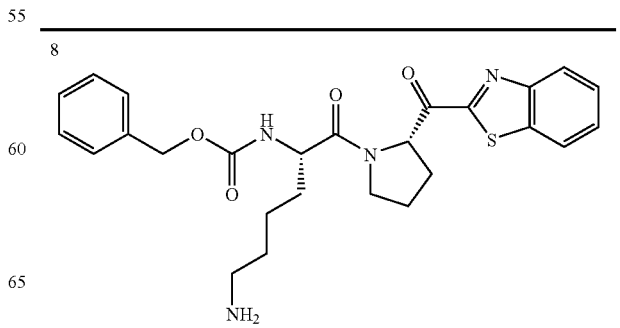

-continued

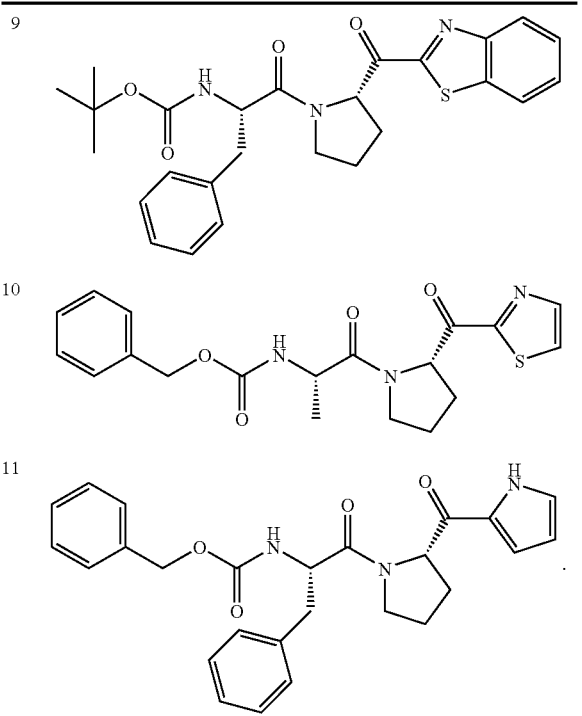

41. A compound according to claim 1 for use as a pharmaceutical.

42. A pharmaceutical composition comprising a compound according to claim 1 together with one or more therapeutically acceptable diluents or carriers.

43. A pharmaceutical composition according to claim 41 for parenteral, enteral or oral administration.

44. A pharmaceutical composition according to 42 which comprises additionally at least one compound selected from the group consisting of QC-inhibitors, LiCl, inhibitors of dipeptidyl aminopeptidases, preferably inhibitors of DP IV or DP IV-like enzymes, NPY-receptor ligands, NPY agonists, ACE inhibitors, PIMT enhancers, inhibitors of beta secretases, inhibitors of gamma secretases, inhibitors of neutral endopeptidase, PDE-4 inhibitors, MAO inhibitors, TNFalpha inhibitors, amyloid protein or amyloid peptide deposition inhibitors, sigma-1 receptor inhibitors and histamine H3 antagonists.

45. A process for preparing a compound of formula (1) according to claim 1 which comprises:

(a) reacting a compound of formula A:

$$W-KCONH-X-CON-Y-COR^x \quad (A)$$

wherein W, K, X and Y are as defined in claim 1 and $R^x$ represents a Weinreb activating group;
or wherein W—K—CO represents allyoxycarbonyl (Abc), t-butyloxycarbonyl (Boc) or benzyloxycarbonyl (Cbz), with a compound of formula B:

$$H-Z \quad (B)$$

wherein Z is as defined in claim 1; or
(b) oxidizing a compound of formula H:

$$W-KCONH-X-CON-Y-CH(OH)-Z \quad (H)$$

wherein W, K, X, Y and Z are as defined in claim 1
wherein W—K—CO represents allyoxycarbonyl (Abc), t-butyloxycarbonyl (Boc) or benzyloxycarbonyl (Cbz);
and if necessary deprotecting the resultant product to obtain a compound of formula (1).

* * * * *

UNITED STATES PATENT AND TRADEMARK OFFICE
CERTIFICATE OF CORRECTION

PATENT NO. : 7,667,044 B2 Page 1 of 1
APPLICATION NO. : 11/290735
DATED : February 23, 2010
INVENTOR(S) : Andre Niestroj et al.

It is certified that error appears in the above-identified patent and that said Letters Patent is hereby corrected as shown below:

On the title page

Related U. S. Application Data item (63) "Continuation-in-part of application No. 11/002,169 filed on Dec. 2, 2004"

should be

(63) --Continuation-in-part of application 11/002,169 filed on Dec. 2, 2004; Continuation-in-part of application No. 10/976,677 filed on Oct. 29, 2004--

Signed and Sealed this

Twentieth Day of April, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,667,044 B2 | Page 1 of 1 |
| APPLICATION NO. | : 11/290735 | |
| DATED | : February 23, 2010 | |
| INVENTOR(S) | : Niestroj et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1012 days.

Signed and Sealed this
Third Day of May, 2011

David J. Kappos
*Director of the United States Patent and Trademark Office*

SEQUENCE LISTING

```
<160> NUMBER OF SEQ ID NOS: 1

<210> SEQ ID NO 1

<211> LENGTH: 24

<212> TYPE: PRT

<213> ORGANISM: Homo Sapiens

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20
```